(12) United States Patent
Raabe

(10) Patent No.: US 12,396,673 B2
(45) Date of Patent: Aug. 26, 2025

(54) SYSTEMS AND METHODS FOR DIFFERENTIATING STIMULUS-EVOKED EVENTS FROM NOISE BY ANALYSIS OF TWO TIME SERIES

(71) Applicant: Winfried Raabe, St. Paul, MN (US)

(72) Inventor: Winfried Raabe, St. Paul, MN (US)

(73) Assignee: DR. WINFRIED RAABE, St. Paul, MN (US)

( * ) Notice: Subject to any disclaimer, the term of this patent is extended or adjusted under 35 U.S.C. 154(b) by 768 days.

(21) Appl. No.: 17/649,164

(22) Filed: Jan. 27, 2022

(65) Prior Publication Data
US 2022/0233131 A1    Jul. 28, 2022

Related U.S. Application Data

(60) Provisional application No. 63/199,843, filed on Jan. 28, 2021.

(51) Int. Cl.
*A61B 5/388* (2021.01)
*A61B 5/00* (2006.01)
*A61B 5/262* (2021.01)
*A61B 5/294* (2021.01)
*A61B 5/397* (2021.01)

(52) U.S. Cl.
CPC .............. *A61B 5/388* (2021.01); *A61B 5/262* (2021.01); *A61B 5/294* (2021.01); *A61B 5/397* (2021.01); *A61B 5/7203* (2013.01); *A61B 5/725* (2013.01); *A61B 2562/0209* (2013.01)

(58) Field of Classification Search
CPC ......... A61B 5/388; A61B 5/262; A61B 5/397; A61B 5/294; A61B 5/7203; A61B 5/725; A61B 2562/0209
See application file for complete search history.

(56) References Cited

U.S. PATENT DOCUMENTS

2020/0078586 A1 *    3/2020   Wijesundara ........... A61B 5/686

OTHER PUBLICATIONS

Raabe, Dr. Winfried, et al., "Median amplitude and frequency analysis of sensory nerve jresponses to intraepidermal stimulation", Journal of Neuroscience Methods 365 109377, (Jan. 1, 2022), 10 pages.
Raabe, Dr. Winfried, et al., "Slowly conducting potentials in human sensory nerves", Journal of Neuroscience Methods 351 109045, (Mar. 1, 2021), 10 pages.

* cited by examiner

*Primary Examiner* — Linda C Dvorak
*Assistant Examiner* — Abigail Bock
(74) *Attorney, Agent, or Firm* — SCHWEGMAN LUNDBERG & WOESSNER, P.A.

(57) ABSTRACT

A method may include obtaining first and second time series (TS1), (TS2) of stimulation data, and a first and second time series of control data. TS1, TS2 may provide a plurality of pairs of data points such that each of the plurality of pairs include corresponding data points from both TS1 and TS2. The obtained time series may be analyzed by applying an algorithm (Alg) to TS1 and TS2 of stimulation data to create an algorithm value corresponding to each of the plurality of pairs of data points. Alg=(|TS1|+|TS2|)/2−|TS1−TS2|. Positive algorithm values for a predetermined period of time (AlgVarTime) may be summed to create a signal. Peak(s) in the signal may be determined, and a conduction velocity may be determined using a latency and a distance between a stimulus electrode and a recording electrode.

22 Claims, 16 Drawing Sheets

$$Alg(TS1, TS2) = \frac{|TS1| + |TS2|}{2} - |TS1 - TS2|$$

TS1: First Time Series
TS2: Second Time Series

TERM 1: Average (Mean) of Rectified TS1 and TS2.

TERM 2: Elimination of TS1 and TS2 With Different Phases (+/−).

Evaluation of similarity of TS1 and TS2 With Same Phase (+/+ or −/−).

Algorithm to Extract Events Having Same Latency and Phase From Two Time Series $$Alg(TS1, TS2) = \frac{|TS1| + |TS2|}{2} - |TS1 - TS2|$$

TS1: First Time Series
TS2: Second Time Series

TERM 1

Average (Mean) of
Rectified TS1 and TS2.

TERM 2

Elimination of TS1 and TS2
With Different Phases (+/−).

Evaluation of similarity
of TS1 and TS2
With Same Phase (+/+ or −/−).

FIG. 5

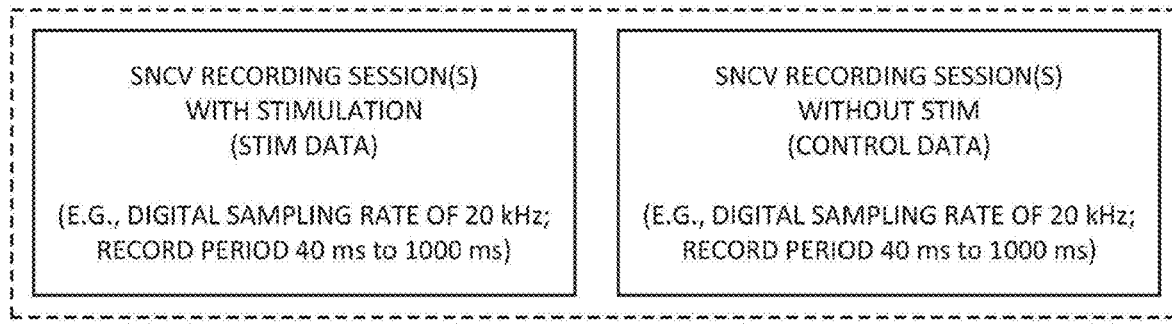
FIG. 14
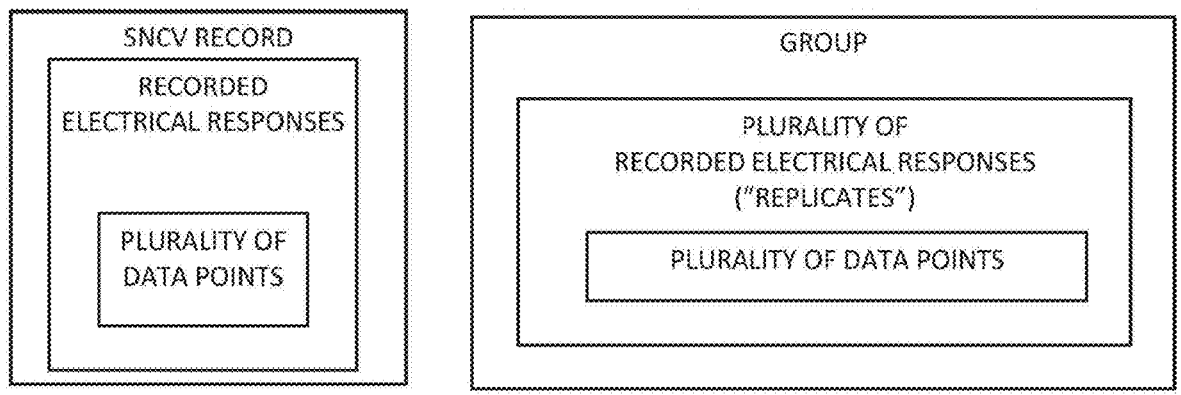
FIG. 15
FIG. 16
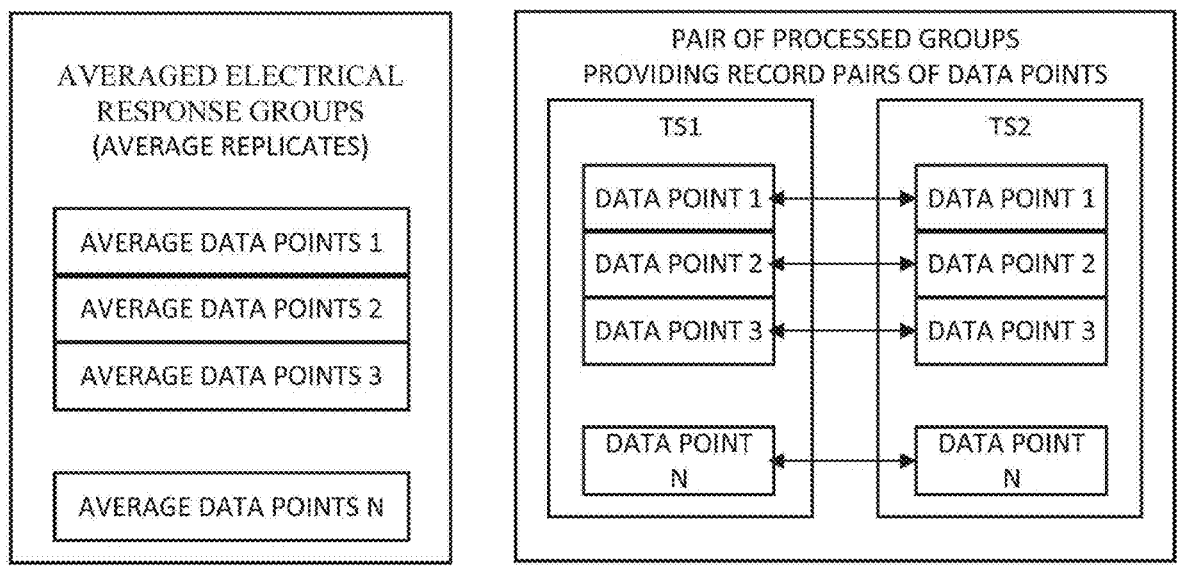
FIG. 17
FIG. 18

SYSTEMS AND METHODS FOR DIFFERENTIATING STIMULUS-EVOKED EVENTS FROM NOISE BY ANALYSIS OF TWO TIME SERIES

CLAIM OF PRIORITY

This application claims the benefit of U.S. Provisional Application No. 63/199,843, filed on Jan. 28, 2021, which is incorporated by reference herein in its entirety.

TECHNICAL FIELD

This document relates generally to systems and methods for differentiating stimulus-evoked events from noise by the analysis of two time series, and more particularly relates to systems and methods for differentiating signs of stimulus-evoked activation of nerve fibers (e.g., Aδ- and C-fibers) from electrical noise by analyzing time series of data obtained from sensory nerve recordings.

BACKGROUND

Human sensory nerves are subdivided into three categories according to their diameter and conduction velocity (CV): (i) Aβ-fibers (6-12 μm and 35-72 m/s) are large, myelinated nerve fibers responsible for the sensation of touch, (ii) Aδ-fibers (1.5-6 μm and 2-30 m/s) are small, myelinated fibers, responsible for the sensation of (immediate) pain and cold, and (iii) C-fibers (0.2-1.5 μm and 0.4-2.0 m/s) are unmyelinated nerve fibers, responsible for the sensation of (throbbing, aching, delayed) pain and warmth/heat.

In current clinical practice, sensory nerve conduction studies only examine Aβ-fibers. Because of their size, Aβ-fibers (6-12 μm in diameter) generate larger potentials than Aδ- and C-fibers (0.2-6 μm in diameter). Because the variation in conduction velocity (35-72 m/s) is only about 2-fold or less, potentials generated by single Aβ-fibers summate and generate potentials large enough (>1 μV) that may be easily recorded with commercially available EMG machines as sensory nerve action potentials (SNAPs). These relatively large potentials can be readily differentiated from electronic background noise generated by the tissue surrounding nerves and the recording equipment, as the electronic noise of preamplifiers is typically ≤0.8 μV. However, Aδ-fibers are anatomically smaller than Aβ-fibers, and C-fibers have even smaller diameters than Aδ-fibers. The electrical signals generated by the activation of Aδ- and C-fibers relate to their diameter. These signals are much smaller (≤10-100 nV) than those of Aβ-fibers. In addition, Aδ- and C-fibers have significant variations in conduction velocities, as Aδ-fibers have a 15-fold variation (2-30 m/s) and C-fibers have a 5-fold variation (0.4-2.0 m/s). These variations in conduction velocity minimize any summation of the already very small single fiber action potentials of Aδ- and C-fibers. Therefore, Aδ-fibers and C-fibers cannot be examined in clinical practice with available nerve conduction study techniques using commercially available EMG machines. Currently, these fibers can only be examined with experimental or very specialized and not commonly available nerve conduction techniques, microneurography, or only indirectly examined with cerebral evoked potentials.

Pain caused by peripheral nerve disease (such as, but not limited to, small fiber neuropathy including diabetic neuropathy) is a clinically significant issue. The vast majority of sensory nerve fibers responsible for the sensation of pain are Aδ- and C-fibers. Therefore, it is desirable to provide techniques to study the function of Aδ- and C-fibers in sensory nerves as a part of routine clinical nerve conduction studies for peripheral nerve disease.

Nerve conduction studies of Aβ-fibers measure amplitude and latency of the sensory nerve action potential elicited by supramaximal sensory nerve stimulation to estimate the number of Aβ-fibers in a nerve and their conduction velocities. Aδ- and C-fibers cannot be studied this way. Stimuli supramaximal for Aβ-fibers are subthreshold for Aδ- and C-fibers. Stimuli strong enough to excite not only Aβ-fibers, but also Aδ- and C-fibers, with conventional stimulus methods/electrodes are likely to cause severe pain.

An alternative technique is the stimulation of only a very limited number of Aδ- and C-fibers in the receptive field of a sensory nerve so that the sensation of pain can be avoided. This can be done with different methods such as two steel pins inserted 3-8 mm apart into the epidermis, or with other devices specifically designed to stimulate only a very limited amount of the terminals of Aδ- and C-fibers in the epidermis (intraepidermal stimulation electrode or concentric planar electrode).

The (non-painful) stimulation of only a very limited amount of Aδ- and C-fibers further decreases the size of their potentials recordable from a nerve. Not only are the potentials small and hardly summate, any summation is further decreased because only a fraction of Aδ- and C-fibers in a nerve are stimulated to avoid pain. (In contrast: Aβ-fiber conduction studies involve the excitation of all Aβ-fibers in a nerve with supramaximal stimulation, the potentials generated by individual Aβ-fibers are much larger than those of Aδ- and C-fibers, and the potentials generated by single Aβ-fibers summate because of little variation in conduction velocities.)

A significant challenge for nerve conduction studies of Aδ- and C-fibers is to differentiate small potentials generated by the excitation of these fibers from baseline/background noise. There is a need for improved systems and methods used to perform nerve conduction studies of Aδ- and C-fibers.

SUMMARY

This document relates generally to improved analysis methods or techniques for differentiating stimulus-evoked events from noise by the analysis of two time series. A time series may be defined as a series of values of a variable, obtained at successive times, with equal intervals (dwell time) between them, and noise may be defined as spontaneous fluctuations of a variable over time. The systems and methods of the present subject matters are believed to be universally applicable to the analysis of two time series obtained in response to a stimulus when the applied stimulus is constant (does not vary) and each application of the stimulus causes or elicits one or more events as defined by latency, duration and phase. Thus, the present subject matter is a technical improvement for monitors to detect stimulus-evoked events. A specialized application of this analysis method is the detection of signs of stimulus-evoked activation of nerve fibers (e.g., Aδ- and C-fibers) and their differentiation from electrical noise. The stimulus may be applied by equipment specifically designed to only stimulate epidermal nerves, and sensory nerve recordings provide the time series for analysis. The equipment for stimulation and recording may be combined as in commercially available EMG machines used for sensory nerve conduction studies in clinical neurophysiology laboratories. Thus, in a particular example, the present subject matter provides a practical application that improves the evaluation of peripheral nerve disease involving pain, particularly small fiber neuropathy, using equipment that is already found in clinical settings.

An example (e.g. "Example 1") includes subject matter (such as a method, means for performing acts, machine readable medium including instructions that when performed by a machine cause the machine to performs acts, or an apparatus to perform). The subject matter may include obtaining a first time series (TS1) and a second time series (TS2) of stimulation data corresponding to recordings that follow identical stimuli of neural tissue, and a first time series and a second time series of control data corresponding to recording that do not follow stimuli of neural tissue. TS1 and TS2 may provide a plurality of pairs of data points such that each of the plurality of pairs include corresponding data points from both TS1 and TS2. The subject matter may further include analyzing the obtained time series by applying an algorithm (Alg) to the first time series (TS1) and the second time series (TS2) of stimulation data to create an algorithm value corresponding to each of the plurality of pairs of data points, wherein $Alg=(|TS1|+|TS2|)/2-|TS1-TS2|$, and the algorithm values include positive algorithm values. The subject matter may further include summing the positive algorithm values for a predetermined period of time (AlgVarTime) to create a signal, determining at least one peak in the signal, and determining a conduction velocity using a latency from the stimulus to the at least one peak in the signal and from a distance between a stimulus electrode used to deliver the stimulus and a recording electrode used to record the electrical responses.

In Example 2, the subject matter of Example 1 may optionally be configured such that the obtaining the first time series (TS1) and the second time series (TS2) of stimulation data includes: stimulating a nerve; recording electrical responses to stimulating the nerve, wherein each of the recorded electrical responses includes a plurality of data points (e.g., sampled data) acquired at equally spaced intervals; and processing the recorded electrical responses to provide the first time series (TS1) and the second time series (T2). The processing of the recorded electrical responses may include separating the recorded electrical responses into groups, where each of the groups includes a plurality of the recorded electrical responses (e.g., replicates), and converting each of the groups into averaged electrical response groups by averaging the plurality of responses in each of the groups. The averaging the plurality of responses may include averaging corresponding ones of the plurality of data points in the plurality of responses. Each of the averaged electrical response groups may provide a plurality of averaged data points that correspond in number to the plurality of data points. The averaged electrical response groups may be the first time series (TS1) and the second time series (TS2) when there are two averaged electrical response groups; or the averaged electrical response groups may be used to provide the first time series (TS1) and the second time series (TS2) when there are more than two averaged electrical response groups.

In Example 3, the subject matter of Example 2 may optionally be configured such that the separating the recorded electrical responses into groups includes separating the recorded electrical responses into two groups, the two groups including a group of odd numbered responses and a group of even numbered responses. The converting each of the groups into averaged electrical response groups includes: averaging corresponding ones of the plurality of data points in the group of odd numbered responses to determine the first time series (TS1); and averaging corresponding ones of the plurality of data points in the group of even numbered responses to determine the second time series (TS2).

In Example 4, the subject matter of Example 3 may optionally be configured such that each of the group of odd numbered responses and the group of even numbered responses includes more than 200 responses to stimulus.

In Example 5, the subject matter of Example 2 may optionally be configured such that the recording electrical responses may include recording a plurality of records, where each of the plurality of records include a plurality of the recorded electrical responses). The separating the recorded electrical responses into groups may include forming unique combinations of two records from the plurality of records to provide the first time series (TS1) and the second time series (TS2).

In Example 6, the subject matter of Example 5 may optionally be configured such that the groups include at least 10 groups of electrical responses to stimulus.

In Example 7, the subject matter of any one or more of Examples 1-6 may optionally be configured such that the stimulating the nerve includes stimulating the nerve at a frequency within a range from 0.5 Hz to 20 Hz using a device configured for stimulation of intraepidermal nerve fibers, and the recording electrical responses to stimulating the nerve includes using subdermal needle to obtain the recording.

In Example 8, the subject matter of any one or more of Examples 1-7 may optionally be configured such that wherein the first time series (TS1) and the second time series (TS2) are analyzed for amplitude using the algorithms (Alg), where the predetermined period of time for summing the positive algorithm values is 0.45 ms In Example 9, the subject matter of any one or more of Examples 1-7 may optionally be configured such that the first time series (TS1) and the second time series (TS2) are analyzed for power spectral density using a Hilbert transformation to determine a power spectra of frequencies for each the averaged groups, where the predetermined period of time for summing the positive algorithm values is 0.45 ms.

In Example 10, the subject matter of any one or more of Examples 1-9 may optionally be configured such that the first time series (TS1) and the second time series (TS2) are analyzed for power spectral density using a Hilbert transformation to determine a power spectra of frequencies for each the averaged groups, where the predetermined period of time for summing the positive algorithm values is 0.45 ms.

In Example 11, the subject matter of any one or more of Examples 1-10 may optionally be configured to further include signal processing each of the first time series (TS1) and the second time series (TS2) for at least one variable to provide at least one pair of processed first time series (TS1) and second time series (TS2) for analysis. The at least one variable may include amplitude or power spectral density. Each of the at least one pair of processed time series TS1 and TS2 may include a plurality of pairs of data points.

In Example 12, the subject matter of Example 11 may optionally be configured such that the signal processing each of the first time series (TS1) and the second time series (TS2) may include at least one of: bandpass filtering to pass frequencies between about 500 Hz to about 1900 Hz; notch filtering to remove excessive frequencies; removing a stimulus artifact; or normalizing data.

In Example 13, the subject matter of any one or more of Examples 1-12 may optionally be configured such that the predetermined period of time is within a range from 0.35 ms to 0.9 ms.

In Example 14, the subject matter of any one or more of Examples 1-12 may optionally be configured such that the predetermined period of time is within a range from 0.40 ms to 0.50 ms.

In Example 15, the subject matter of any one or more of Examples 1-12 may optionally be configured such that the predetermined period of time is 0.45 ms.

In Example 16, the subject matter of any one or more of Examples 1-15 may optionally be configured to further include comparing the at least one peak in the signal to a threshold value to identify action potentials.

In Example 17, the subject matter of Examples 1-16 may optionally be configured such that the threshold value is determined using the first time series and the second time series of control data that do not follow stimuli of neural tissue.

In Example 18, the subject matter of Examples 1-17 may optionally be configured to further include applying the algorithm (Alg) to the first time series (TS1) and the second time series (TS2) of control data to create a control algorithm value corresponding to each of the plurality of pairs of data points, wherein the threshold is above or equal to 99% of a maximum control algorithm data.

In Example 19, the subject matter of Examples 1-18 may optionally be configured to further include receiving a file from a clinical group that includes at least one clinician, wherein the file includes recordings of electrical responses to stimulating a nerve recorded using an EMG system, and the first time series (TS1) and the second time series (TS2) of stimulation data are obtained using the file, the method further comprising reporting the conduction velocity to the at least clinician.

In Example 20, the subject matter of Example 19 may optionally be configured such that the reporting the conduction velocity includes reporting distributions of conduction velocities determined using the signal created by summing the positive algorithm values for the predetermined period of time (AlgVarTime).

In Example 21, the subject matter of Examples 19-20 may optionally be configured to further include entering a license granting permission to upload the file and to receive the reporting of the conduction velocity.

An example (e.g. "Example 22") includes subject matter comprising a non-transitory machine-readable medium including instructions, which when executed by a machine, cause the machine to implement a method. The method may include the subject matter of any one or more of Examples 1-21.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 5 illustrates the design of the algorithm Alg to detect stimulus-evoked events with the same latency and same phase in two time series.

FIG. 14 illustrates sensory nerve conduction velocity (SNCV) recording sessions to provide stimulation data ("STIM DATA") and SNCV recording sessions to provide Control Data ("CTRL DATA").

FIG. 15 illustrates an SNCV record, recorded by EMG equipment; and the SNCV record with STIM DATA includes recorded electrical responses to stimuli, whereas the SNCV record with CTRL data includes recorded electrical activity for a corresponding period of time without stimuli.

FIG. 16 illustrates a group that includes a plurality of recorded electrical responses, where the recorded electrical responses include a plurality of data points.

FIG. 17 illustrates averaging of the replicates, or electrical responses by corresponding data points for each of the replicates by averaging data points 1, averaging data points 2, averaging data points 3, etc., which converts the groups into an averaged electrical response group.

FIG. 18 illustrates a first time series (TS1) and a second time series (TS2), which provide record pairs of data points (e.g., a first record pair: Data Point 1 in TS1 and Data Point 1 in TS2; a second record pair: Data Point 2 in TS2 and Data Point 2 in TS2, and the like).

DETAILED DESCRIPTION

Figure 1:
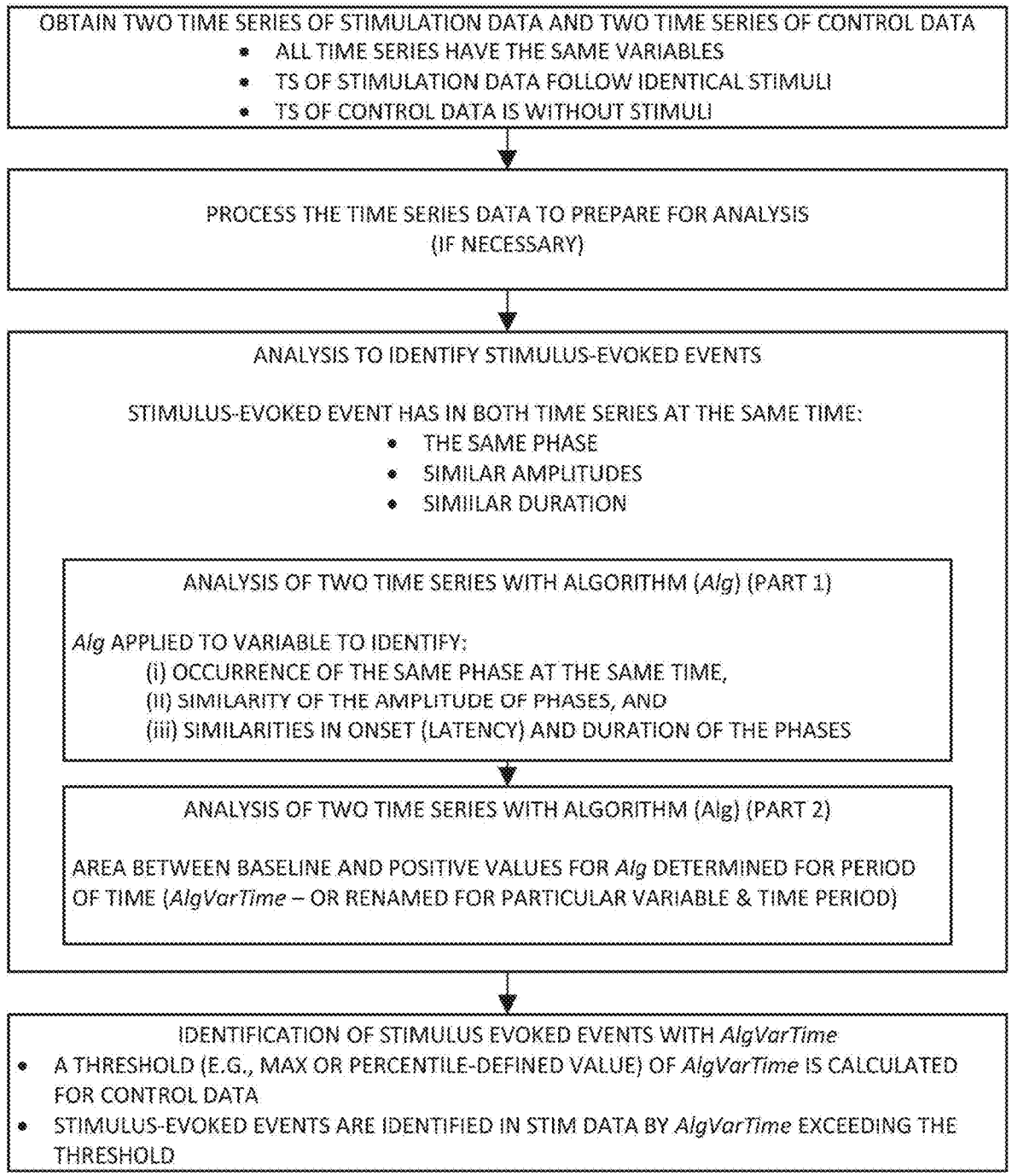
FIG. 1 illustrates, by way of example and not limitation, general principles for the detection of stimulus-evoked events by the analysis of two time series.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and other changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Many diseases that affect peripheral nerves are associated with pain. Examples of such disease include diabetic peripheral neuropathy and nerve injuries. Aδ- and C-fibers carry the sensations of pain. For the treatment of pain it is important to understand what causes the symptom and to direct the treatment to that cause.

Conventionally, clinicians may perform a nerve biopsy to assess the anatomical integrity of the these fibers. However, this invasive procedure does not permit conclusions as to the physiological function of the nerve. For example, a skin biopsy is performed to evaluate the anatomical integrity of Aδ- and C-fiber in the epidermis, but does not evaluate their functional integrity. Furthermore, a skin biopsy cannot differentiate between Aδ- and C-fibers whereas the present subject matter can differentiate between these fibers.

Previous attempts to assess the function of a peripheral nerve involve sensory nerve conduction studies. These previous attempts only evaluate the Aβ-fibers, which are only 1/10th of the fibers in a sensory nerve. The present subject matter expands the neurophysiological evaluation of sensory nerves to include the remainder 9/10th of sensory nerve fibers (Aδ- and C-fibers) which were previously not evaluated. A significant challenge for nerve conduction studies of Aδ- and C-fibers is to differentiate small potentials generated by the excitation of these fibers from baseline/background noise. The present subject matter accomplishes this through the use of an algorithm that compares two time series obtained after application of two identical stimuli to the terminals of Aδ- and C-fibers in the epidermis, and identifies events when both time series show features compatible with the generation of one or more single fiber action potentials. The latencies of these and the distance between stimulation and recording points permit the calculation of conduction velocities. The distribution of the conduction velocities identified by the algorithm can be represented in a histogram showing how many fibers conduct in the range for Aδ-fibers, 2-30 m/s and the range for C-fibers, 0.4-2.0 m/s.

The present subject matter relates to systems and methods for extracting potentials generated by Aδ-fibers and C-fibers from recordings obtained with commercial EMG machines and commercial recording equipment from human sensory nerves. Equipment and methods available in clinical neurophysiology laboratories may be used to perform near nerve recordings from human sensory nerves, which the present subject matter enables to be used to assess sensory nerve fibers to determine whether the pain conveying Aδ- and C-fiber are decreased in a nerve.

With suitable stimulation and recording techniques as well as an algorithm-based data analysis disclosed herein, commercially available EMG equipment can be used to study pain (and temperature) conducting Aδ-fibers without the experience of pain within a reasonable time frame in the clinical neurophysiology/EMG laboratory. The methods described in this study may add to the clinical electrophysiological evaluation of peripheral nerve disease involving pain, particularly small fiber neuropathy.

EMG machines and commonly practiced sensory nerve recording techniques may be used to record sensory nerve potentials conducting at speeds less than 30 m/s. By way of example and not limitation, two-channel EMG systems, Synergy N2 or T2 (Natus Medical), may be used for stimulation and recording. Furthermore, by way of example and not limitation, the skin innervated by the superficial radial, superficial fibular and sural nerves may be stimulated at 1-20 Hz with an electrode for intraepidermal stimulation. The stimulus may be delivered using single rectangular pulses with an amplitude within a range of 0.03-1.00 mA and a duration within a range of 0.2-0.5 ms. The perception threshold for the stimuli may be within a range of 0.09-0.27 mA. At perception threshold, the stimuli with these parameters may be perceived as tiny pin-pricks rather than pain.

As will be discussed in more detail below, a large number of responses to a non-noxious stimulus may be averaged. The applied stimulus is constant (including constant stimulation intervals), and the responses are acquired at equally spaced intervals ("dwell time"≤0.05 ms). The individual responses as well as their average are time series. The number of replicates for an average may vary between 100 and 5000. It is believed that potentials generated by Aδ- (and C-) fibers will occur within a precise time window after each stimulus. The signal generated by the-activation of Aδ- (and C-) fibers is extracted from two time series using the algorithm Alg, shown in FIG. 5. This algorithm weighs the variable of the time series (e.g., the electrical potential) with the same phase (e.g., negative or positive) by their difference in amplitude. It is more likely that potentials are generated by the same source, i.e., Aδ- (and C-) fibers, when the potentials are higher and there is less difference in amplitude. Since single fiber action potentials of Aδ- (and C-) fibers have a duration of about 0.5 ms, the measurement of Alg is extended to a 0.45 ms period of positive Alg data. This modification of Alg by time (AlgVarTime) is called ALG045, to indicate a signal generated by one or more single fiber action potentials of Aδ- (and/or C-) fibers.

EMG equipment may output recordings of electrical potentials acquired at equally spaced intervals, i.e., time series, as data files in an exportable format (e.g. .txt file or CSV file). The processing system (e.g., computer or Software As A Service) may be configured to receive the file and process the recordings/time series to evaluate the latencies of stimulus evoked events. These latencies and the distances between stimulation and recording sites are then used to calculate the conduction velocities of Aδ- (and C-) fibers. The result of the calculations may be output in a manner to provide desired information to the user. For example, the output may be output as a human readable report in a word processor form (e.g., MS Word document) or Portable Document Format (pdf) or other output.

FIG. 1 generally illustrates principles for the detection of stimulus-evoked events by the analysis of two time series with the algorithm Alg and its application for a particular period of time called AlgVarTime. The time period for AlgVarTime is determined by the stimulus-evoked event to be detected. AlgVarTime may be renamed reflecting the identity of variable of the time series and the specific duration of the event to be detected.

Figure 2:
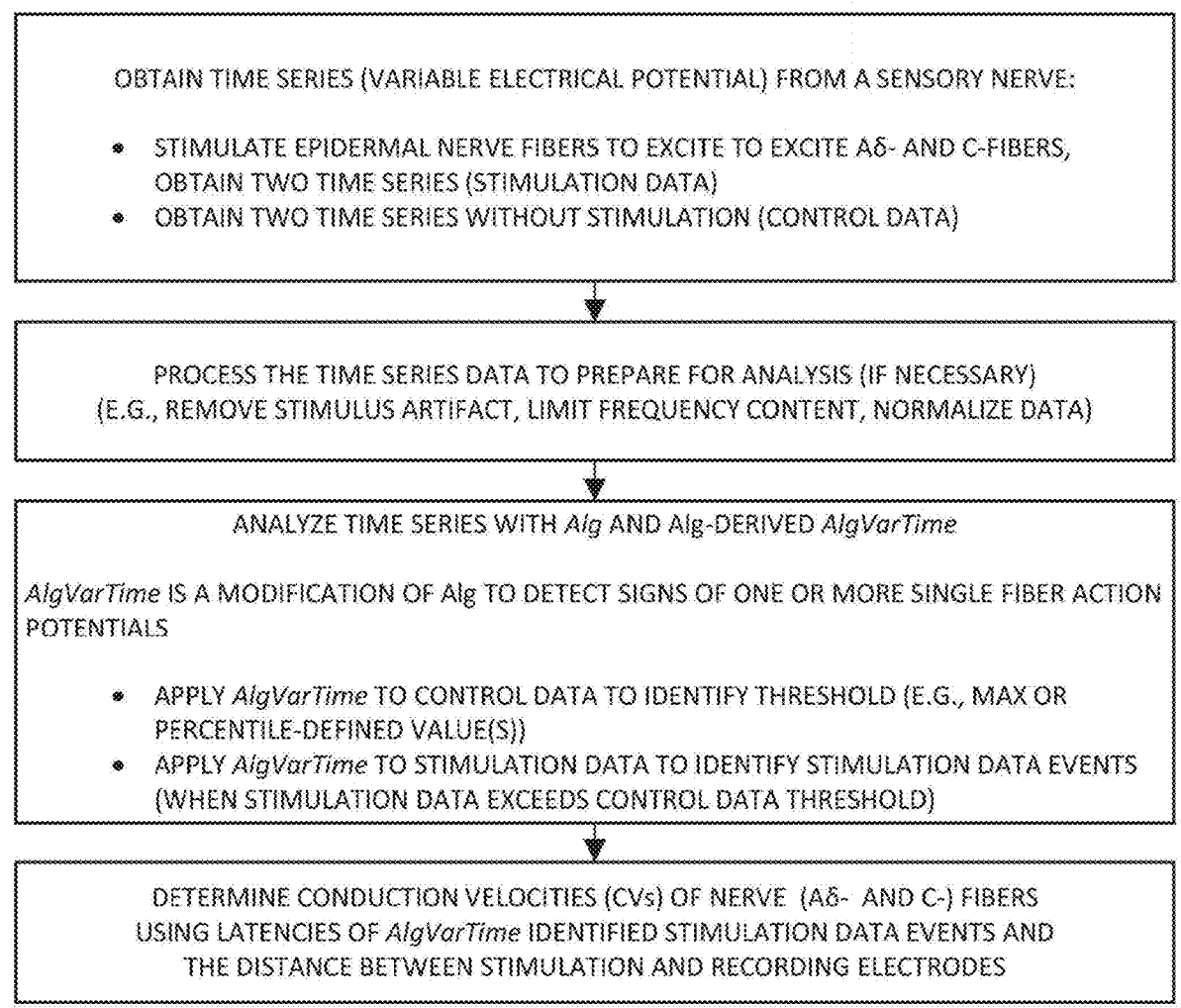
FIG. 2 illustrates principles for the detection of stimulus-evoked events by analysis of two time series as applied to the identification of nerve fiber (Aδ- and C-fiber) conduction velocities in a sensory nerve.

FIG. 2 illustrates, by way of example and not limitation, an embodiment of a method for evaluating the function of slow conducting nerve fibers, Aδ- and C-fibers. The principles of the detection of stimulus-evoked events by analysis of two time series is applied to the identification of nerve fibers (Aδ- and C-fibers) in a sensory nerve. The algorithm Alg is applied to a particular variable for a particular period of time. This modification of Alg is called AlgVarTime. The latter is specifically designed to detect signs of single fiber action potentials. AlgVarTime in stimulation data exceeding a predefined value of AlgVarTime of control data indicates a stimulation-evoked event. The latency of this event may be used for the calculation of a conduction velocity. Because of the wide range of conduction velocities of Aδ- and C-fibers, 0.4-30 m/s, the conduction velocity may be used to indicate the presence of one or more Aδ- and/or C-fibers in a sensory nerve.

Figure 3:
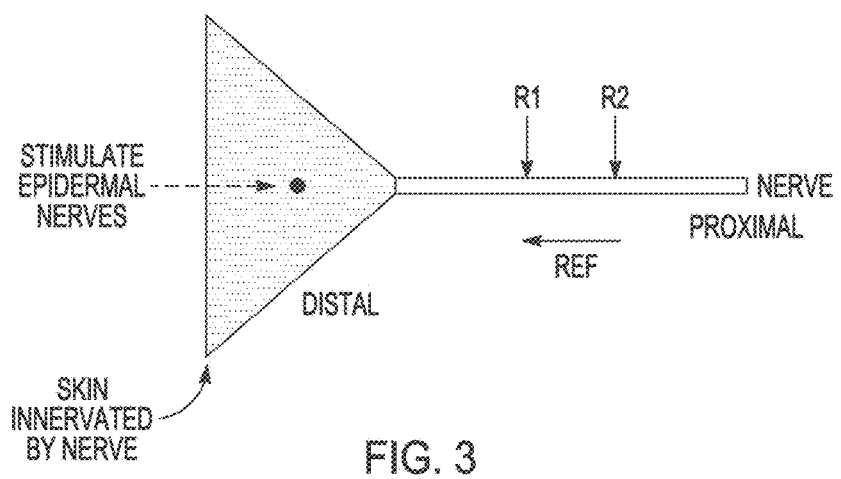
FIG. 3 illustrates stimulation and recording methods to obtain time-series containing events generated by Aδ- and C-fibers.

FIG. 3 provides, by way of example and not limitation, a schematic representation of stimulation and recording methods to obtain time series containing events generated by Aδ- and C-fibers. Methods for stimulation can vary. For example, the stimulation methods may use two steel pins inserted into the epidermis, an intra-epidermal stimulation electrode, or a concentric planar electrode. Methods for recording time-series can vary. For example, the recording methods may include monopolar recording of a near-nerve electrode vs. a distant reference electrode, shown in FIG. 3 with arrows labeled "Record" and "Ref" as shown here (or bipolar recording with one near-nerve electrode recording vs. another near-nerve electrode, not shown).

Figure 4:
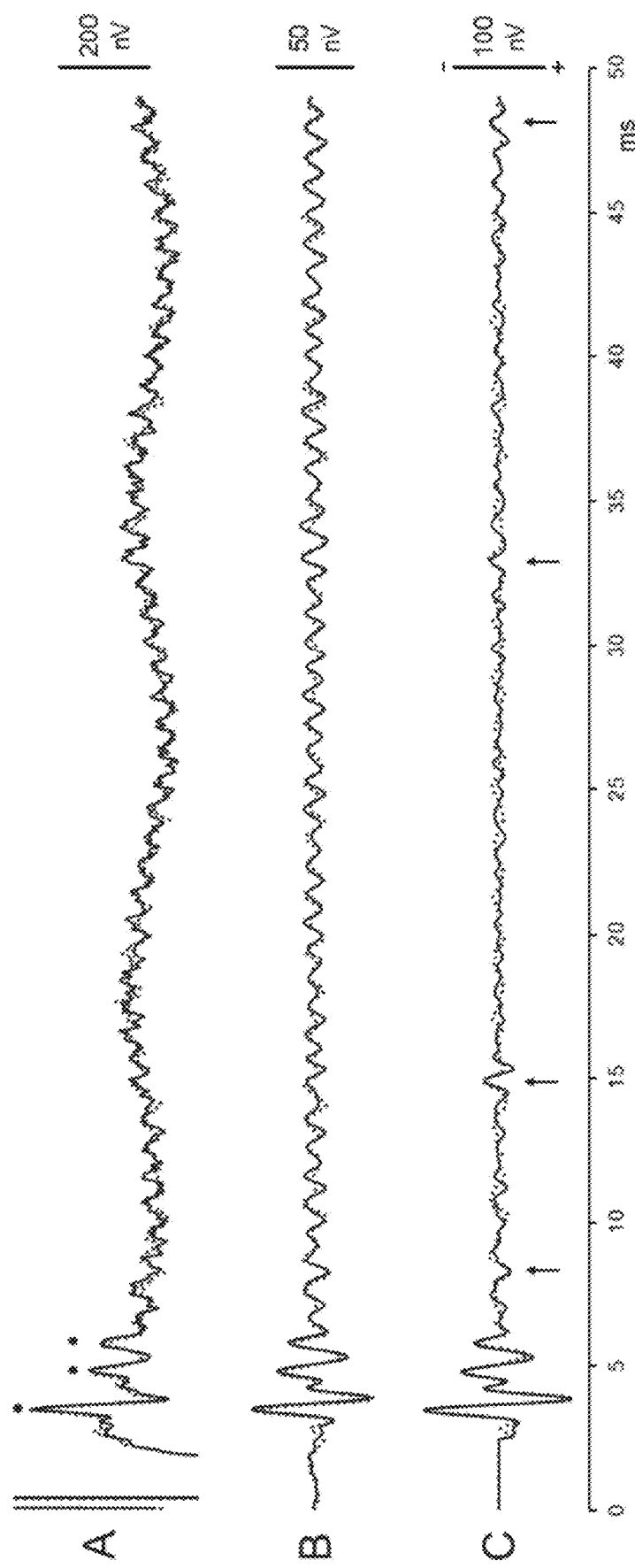
FIG. 4 illustrates, by way of example and not limitation, processing of time series data to be suitable for analysis with Alg and AlgVarTime.

FIG. 4 illustrates, by way of example and not limitation, processing of time series data to be suitable for analysis with Alg and AlgVarTime. In tracings A, time series 1 and 2 (solid line and dotted tracings) have been obtained from a sensory nerve after stimulation of intra-epidermal nerve fibers in the cutaneous area innervated by the superficial radial nerve (here stimulation of skin over 1st dorsal interosseus muscle, recording from superficial radial nerve at distal forearm). Interval/dwell time period for time series is 0.05 ms. In this embodiment, the variable of the time series is the electrical potential, and time series 1 and 2 each are the average of 3000 replicates. Dots in FIG. 4A identify stimulus-evoked events visually discernable from noise by the overlap of time-series 1 with time series 2 and their signal-to-noise ratio≥2.25. Tracings B illustrate time series 1 and 2 after elimination of the stimulus artifact with exponential fits to the periods 3.5-20 ms and 1-3 ms and by substitution of a straight line from 0 nV at 0.00 ms to the particular potential at 2.5 ms in time-series 1 and 2. Thereafter, application of a bandpass filter 500-1900 Hz and normalization of records to a standard deviation of 4 nV for the period 10-48.5 ms. Tracings C illustrate time-series 1 and 2 after application of a notch filter to eliminate the frequency visibly contaminating time-series 1 and 2, and thereafter, repeat normalization of records to a standard deviation of 4 nV for the period 10-48.5 ms. The arrows point to stimulus-evoked events identified by application of the algorithms Alg/AlgVarTime to the electrical potential for a 0.45 ms period and called ALG045. See also FIG. 7.

FIG. 5 illustrates the design of the algorithm Alg to detect stimulus-evoked events occurring in two time series with the same latency and same phase. Positive values for Alg indicate similarities in amplitude and phase at the same time. The first term of Alg uses the absolute values of TS1 and TS2, which rectifies TS1 and TS2 and calculates the average (mean) of TS1 and TS2, creating a positive average for all three TS1/TS2 phase combinations: +/+, −/− and +/−. This term of Alg provides the first evaluation of the similarity of TS1 and TS2, where a low average indicates that either TS1 and TS2 are not similar or TS1 and TS2 are very small. The second term of Alg eliminates periods of TS1 and TS2 with different phases (+/−), and provides a second evaluation for the similarity of phase congruent (+/+) and (−/−) periods of TS1 and TS2. The impact of this term of Alg depends on the ratio of the average of TS1 and TS2, i.e., the first term of Alg, to the second term of Alg, i.e., the difference between TS1 and TS2.

The algorithm Alg may be modified/extended into another algorithm called AlgVarTime, which calculates the area between positive values for Alg and the zero baseline for a specific time period. AlgVarTime may be renamed to reflect the variable of the time series and the period of time for the calculation of the area. For example, when the variable is the amplitude of the electrical potential and the time period is 0.45 ms to detect signs of single fiber action potentials, the algorithm AlgVarTime may be called "ALG045".

Figure 6:
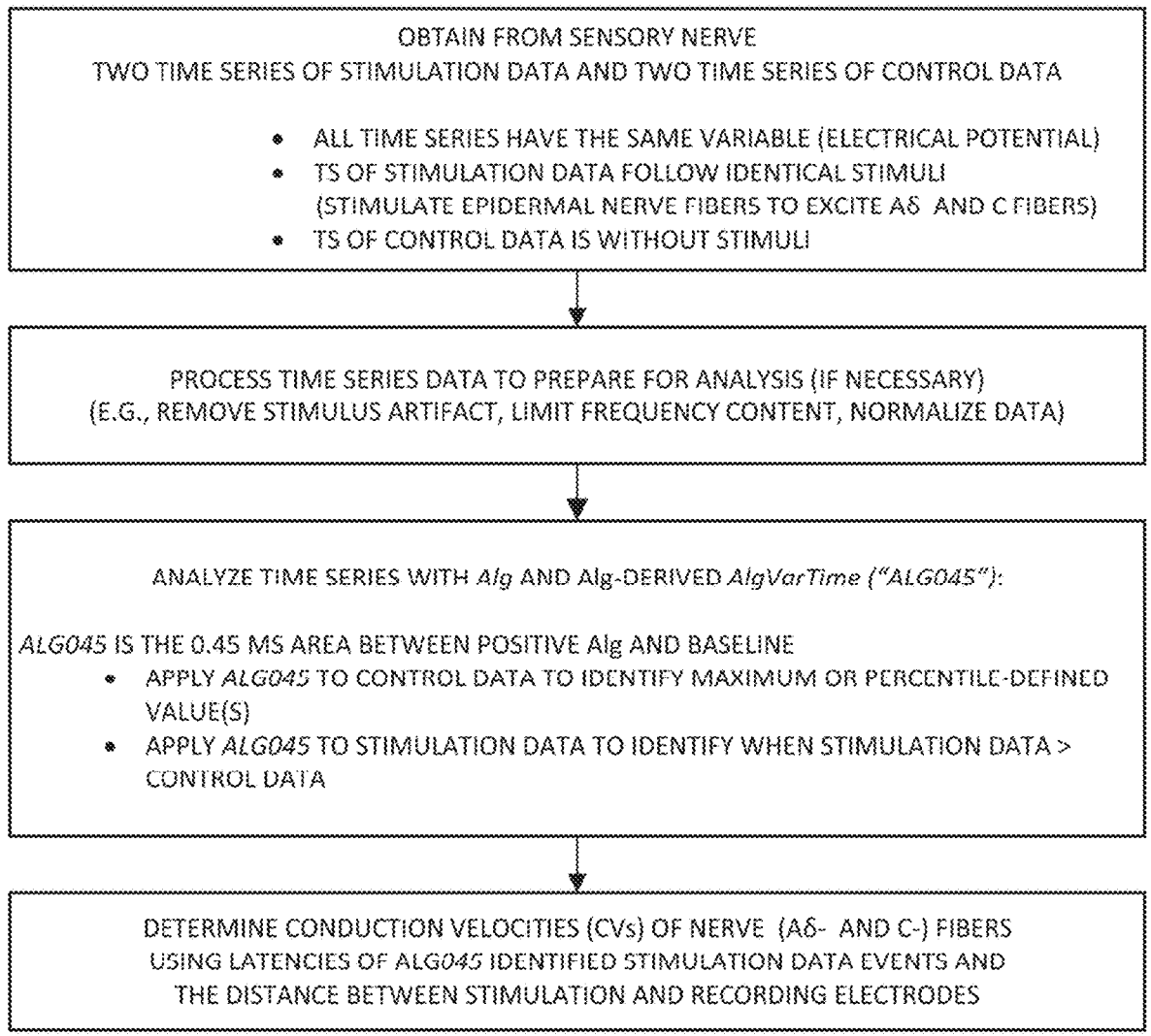
FIG. 6 illustrates the application of the algorithms Alg and AlgVarTime to identify events generated by the activation of one or more single nerve fibers (Aδ- and/or C-fibers) in two time series, TS1 and TS2.

FIG. 6 illustrates the application of the algorithms Alg and AlgVarTime to time series recorded from sensory nerves to identify the latencies of potentials generated by Aδ- and C-fibers for the purpose of the calculation of conduction velocities. Two time series are obtained with stimulation (stimulation data) and two time series are obtained without stimulation (control data). The variable of the time series is the electrical potential. The area between positive Alg data and the zero Alg baseline is calculated for a 0.45 ms period. This period is chosen because the dominant, negative phase of single fiber action potentials of Aδ- and C-fibers has a duration of ≈0.5 ms. AlgVarTime is renamed "ALG045" to indicate its application to the electrical potential for a specified time period. ALG045 of stimulation data greater than the maximum (or particular percentile) of ALG045 for control data identifies the latencies used for the calculation of conduction velocities from the distance between stimulus and recording electrodes.

Figure 7:
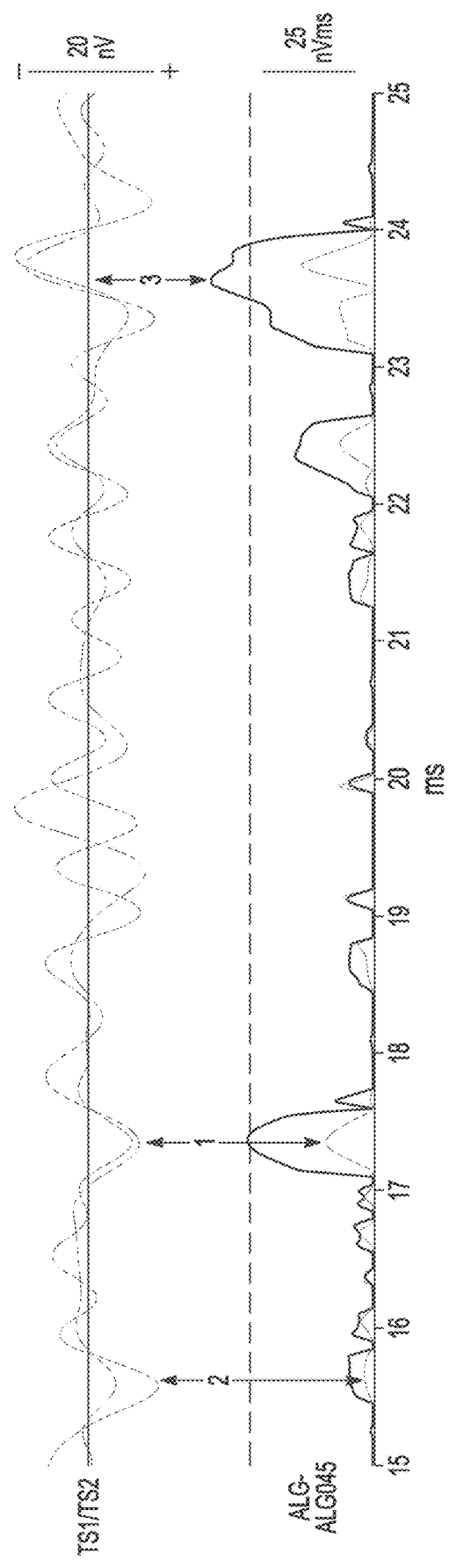
FIG. 7 illustrates, by way of example and not limitation, an application of the algorithms Alg and AlgVarTime to identify stimulus-evoked events generated by the activation of one or more single Aδ- and C-fibers in two time series, TS1 and TS2, obtained after stimulation.

FIG. 7 illustrates, by way of example and not limitation, an application of the algorithms Alg and AlgVarTime to identify stimulus-evoked events generated by the activation of one or more single Aδ- and C-fibers in two time series, TS1 and TS2, obtained after stimulation. In the illustrated embodiment, the variable for TS1 and TS2 is the electrical potential (in nV). Interval/dwell time period for time series is 0.05 ms. The upper tracings show time series TS1 and TS2

(solid and dotted tracings) and 0 nV baseline (straight line), and the lower tracings show the algorithm Alg (dotted trace line) applied to TS1 and TS2 and the 0.45 ms area between Alg and baseline, i.e., AlgVarTime named "ALG045" (solid trace line). The duration of 0.45 ms for AlgVarTime is chosen to reflect the duration of the dominant, negative phase of single fiber action potentials. The horizontal dashed line indicates the $99.5^{th}$ percentile of ALG045 derived from two time series without stimulation (controls). Arrows 1 identify two potentials that largely overlap in latency, phase, amplitude and duration creating distinct peaks of Alg and ALG045, compatible with the same set of single fiber action potentials recorded by time series 1 and 2. ALG045 exceeds the dotted line indicating that the event identified is significantly different compared to control time series. Arrows 2 point to a section of TS1 and TS2 with about the same average as TS1 and TS2 labeled by arrows 1. Here, the large difference between TS1 and TS2 decreases Alg and ALG045 to sizes not different from those seen with ALG045 of control TS1 and TS2 (no stimulation). Arrows 3 illustrate that the peak of ALG045 may not always have the exact same latency as the peak of Alg, but may still identify an event generated by single fiber action potentials.

ALG045 is applied to a pair of stimulation data (stimulation time series 1 and 2, stimulation TS1/TS2) and to a pair of control data (control time series 1 and 2, control TS1/TS2). The maximum or a percentile-defined value of ALG045 is determined for control data. This "Control ALG045" has to be exceed by ALG045 of stimulation data ("Stimulation ALG045") to indicate that Stimulation ALG045 detects a stimulus-evoked event.

The latencies of the stimulus-evoked events identified by Stimulation ALG045 may be used to calculate the conduction velocities of the events by dividing the distance between stimulus and recording electrode by the latency.

Figure 8:
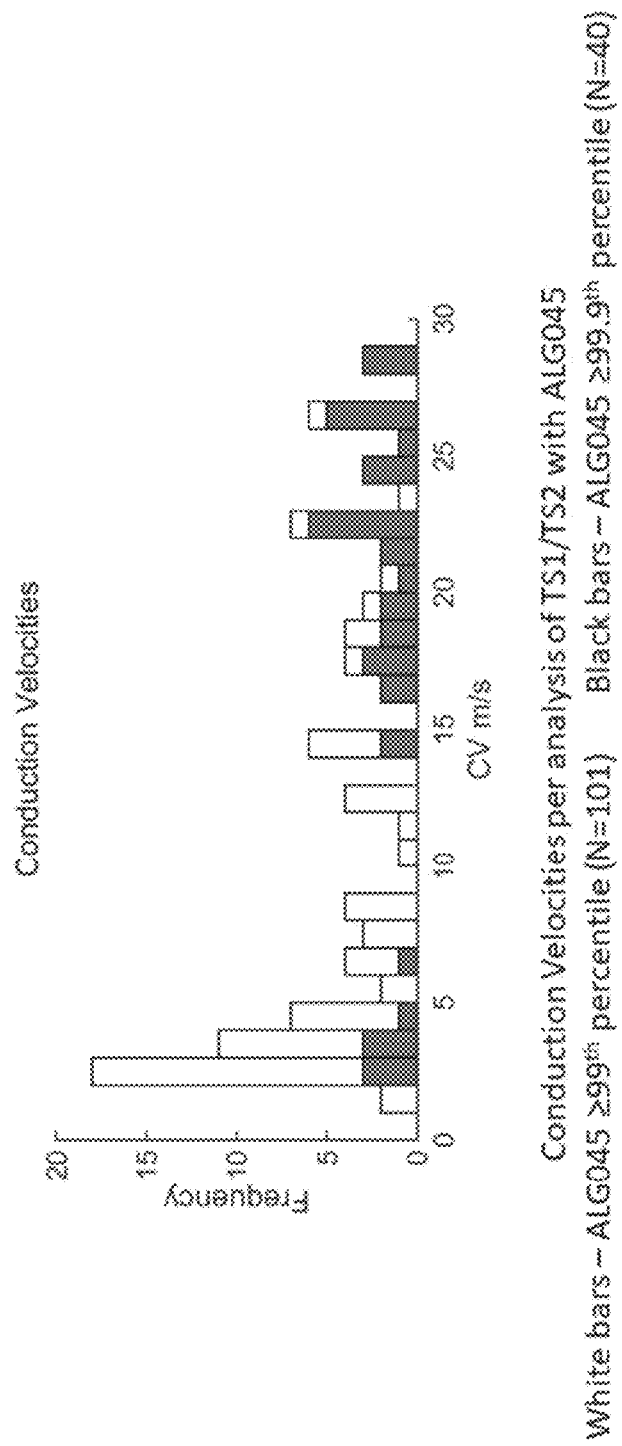
FIG. 8 illustrates, by way of example and not limitation, distributions of Aδ-fiber conduction velocities (CVs) of stimulus-evoked events detected by ALG045 in 82 monopolar TS1/TS2 data from superficial radial, superficial fibular and sural nerves.

FIG. 8 illustrates distributions of Aδ-fiber conduction velocities (CVs) derived from stimulus-evoked events detected by ALG045 in 82 monopolar TS1/TS2 stimulation data from superficial radial, superficial fibular and sural nerves. The white bars represent ALG045≥$99^{th}$ percentile of Control ALG045 (N=101); and the black bars represent ALG045≥$99.9^{th}$ percentile of Control ALG045 (N=40).

The algorithms Alg and AlgVarTime may not only be applied to the electrical potential as variable of two time series but also to other variables recorded with a time series. For example, power spectral density is a variable that can be derived from near nerve recordings of the electrical potential. The power spectral density is a variable determined by the frequency content of the electrical potential recorded. Alg and AlgVarTime can be applied to the power spectral density. AlgVarTime may be renamed "PS045" to indicate the variable of the time series is the power spectral density and the time for calculation of PS045 is 0.45 ms, which is the time for the identification of events generated by single fiber action potentials.

Figure 9:
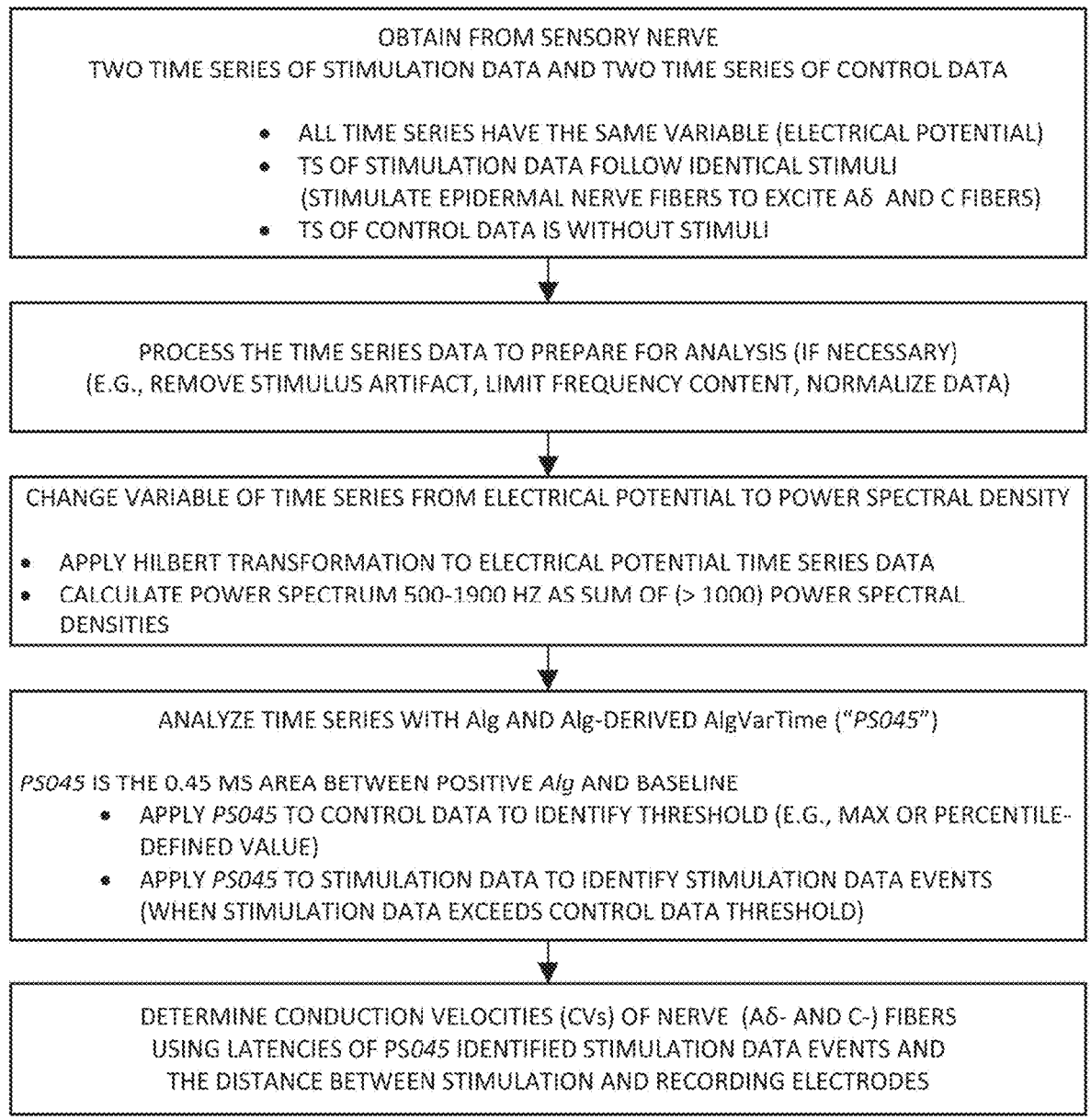
FIG. 9 illustrates the application of the algorithms Alg and AlgVarTime to the power spectral density as variable of two time series.

FIG. 9 generally illustrates principles of the detection of stimulus-evoked events by power spectral density analysis (spectral analysis) of two time series. The time series may be recorded with the electrical potential as variable. Thereafter, the time series may be processed in preparation for analysis as outlined in FIG. 4. The Hilbert transformation may be applied to the processed data. The Hilbert transformed data may be used to obtain the power spectral densities of 500-1900 Hz at 1-2 Hz intervals. The sum of the power spectral densities may be calculated for each time point of the two time series. Alg may be obtained for the two time series, and the 0.45 ms area between baseline (Alg=0) and positive Alg data, i.e., AlgVarTime. The latter may be relabeled "PS045" to indicate the nature of the variable of the time series analyzed, i.e., the power spectral density, and the period of time used for analysis.

Figure 10:
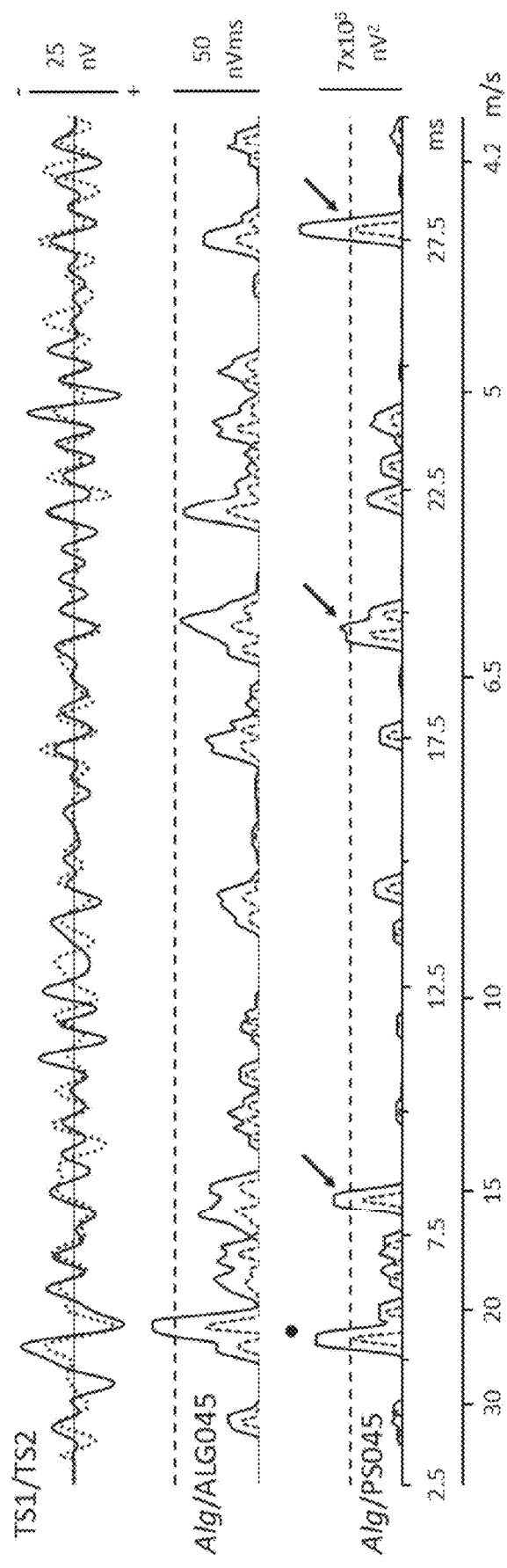
FIG. 10 illustrates the application of Alg and AlgVarTime to the electrical potential of two time series, ALG045, as well as the electrical potential-derived power spectral density, PS045.

FIG. 10 illustrates, by way of example and not limitation, an application of Alg and AlgVarTime to two time series, TS1 and TS2, obtained with stimulation at 20 Hz as alternate averages, cf. [0085]. Upper tracings: solid and dotted lines are tracings of TS1 and TS2. Interval/dwell time period for time series is 0.05 ms. TS1 and TS2 data were processed as shown in FIG. 4. Middle tracings: A/g/AGL045 illustrate Alg (dotted tracing) applied to the electrical potential (in nV) of TS1 and TS2, and ALG045 (solid tracing) is an example of AlgVarTime, i.e., the 0.45 ms area between positive Alg and baseline. Bottom tracings: Alg/PS045 illustrate Alg applied to the power spectral densities of TS1 and TS2, dotted tracing. AlgVarTime, i.e., the 0.45 ms area between positive Alg and baseline, PS045, is shown as solid tracing. As represented by the dot (•), the same event is detected by ALG045 and PS045. Arrows indicate that PS045 may detect stimulus-evoked events not detected by ALG045. The detection of stimulus-evoked events may be enhanced by the use of one or more variables for a pair of time series as illustrated by the use of ALG045 and PS045. See also FIG. 13.

To confirm that the stimulus-evoked events detected by ALG045 and PS045 are indeed generated by single-fiber action potentials of Aδ- (or C-) fibers, one can investigate the effects of a local anesthetic on the stimulus-evoked events identified by ALG045 and PS045. If the local anesthetic abolishes or significantly diminishes the stimulus-evoked events, it can be concluded that these events were generated by the excitation of Aδ- (or C-) fibers.

Figure 11:
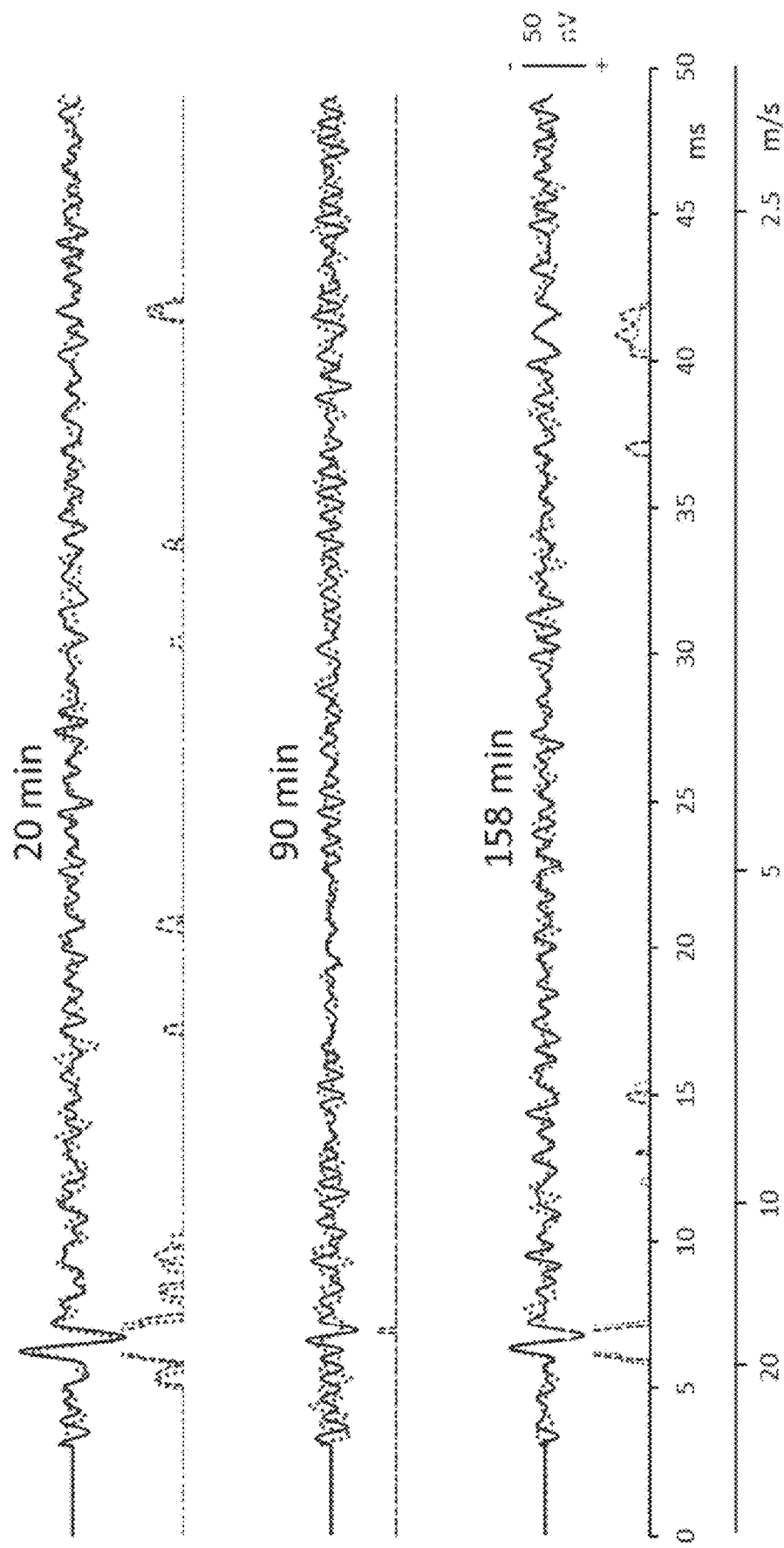
FIG. 11 illustrates that ALG045 and PS045 detect stimulus-evoked responses generated by the activation of nerve fibers, here Aδ-fibers. Lidocaine, a nerve excitation blocking agent reversibly abolishes the stimulus-evoked events detected by ALG045 and PS045.

FIG. 11 illustrates the effects of lidocaine cream on stimulus-evoked responses detected with ALG045 and PS045. Lidocaine reversibly abolishes/diminishes stimulus-evoked responses detected by ALG045 and PS045. Lidocaine may be applied to the skin innervated by the superficial peroneal nerve just prior to placement of the stimulus electrode, and a near-nerve recording from the superficial peroneal nerve at the ankle may be taken. Three sets of tracings are shown, labeled 20 min, 90 min and 158 min. In each set, the upper tracings are the stimulus-evoked time series TS1 and TS2, each an average of 2000 replicates (solid and dotted tracings). The lower tracings are ALG045 and PS045>control ALG045/PS045 (dashed and dotted tracings). 20 minutes after application of lidocaine cream ALG045 and PS045 detect several stimulus-evoked events. 90 minutes after application of lidocaine cream, only one minor stimulus-evoked event is detected by ALG045, and no stimulus-evoked event is detected by PS045. 158 minutes after application of lidocaine cream, ALG045 and PS045 detect again several stimulus-evoked responses. Calibration bar on bottom is for conduction velocity in m/s. The effects of lidocaine, a local anesthetic, on stimulus-evoked responses detected with ALG045 and PS045 demonstrate that ALG045 and PS045 detect stimulus-evoked events that are generated by the excitation of nerve fibers (in FIG. 11, Aδ-fibers). (TS1 and TS2 acquired with 20 Hz stimulation as alternate averages, cf. [0085].)

Only stimulus electrodes exciting a very limited portion of epidermal nerve fibers should be used to avoid pain. The electrodes (electrode configurations) include: 2 steel pins inserted 3-5 mm apart into the epidermis, the intra-epidermal stimulation electrode and the concentric planar electrode. Stimuli delivered at frequencies of 0.5-20 Hz may be used to detects events generated by the excitation of Aδ- and/or C-fibers. Stimuli delivered at frequencies of 0.5-2 Hz may be used to detect events generated by the excitation of C-fibers. The electrical stimuli may include rectangular pulses of 0.03-1.00 mA with a duration of 0.2-0.5 ms. The stimuli are adjusted so that they are perceived as tiny pin-pricks but not pain. Near-nerve recordings may be obtained with subdermal needles. For example, action potentials in the superficial fibular nerve, sural nerve or superficial radial nerve may be sensed. Distances between intraepidermal stimulation electrode and most distal recording electrode may be, by way of example and not limitation, within a range of 50-150 mm.

Control time series (recording activity without stimulation) and stimulation time series (recording responses to stimulation) may be obtained. The data acquisition period for control and stimulation time series may vary from 50 ms to >200 ms. The data acquisition period is determined by the rate of stimulation. Stimulation with 20 Hz limits the data acquisition period to 50 ms. Stimulation with 0.5 Hz permits a data acquisition period of 2000 ms. The actual data acquisition period may be determined by the commercial EMG machine used. Some commercial EMG machines are limited to the acquisition of a 200 ms period of digital data with a dwell time of <0.05 ms. In principle, control and stimulation time series may be obtained as time series following a single trigger for data acquisition (control time series) or single stimuli (stimulation time series). Control and stimulation time series for the detection of stimulus evoked Aδ- and C-fiber events may be obtained as averages of N successive replicates, N ranging from 100-5000. On the EMG systems the bandpass may be set to 500-3000 Hz for data acquisition.

With suitable data acquisition and analysis techniques, commercial EMG equipment can be used to obtain data on slowly conducting potentials in human sensory nerves with CVs within a range between 0.4-30 m/s. The only equipment that generally would not be found in a clinical EMG laboratory are electrodes specifically designed to stimulate intraepidermal nerve fibers (intraepidermal stimulation electrode, concentric planar electrode). Stimulation of epidermal nerve fibers can also be done with 2 steel pins, subdermal needles, inserted into the epidermis. Subdermal needles are equipment routinely used in clinical neurophysiology labs The equipment used for data acquisition has to be able to acquire and store data in digital format with a dwell time of ≤0.05 ms, corresponding to a digitization frequency of ≥20 kHz.

Stimulation and control time series data may be obtained in two (or more) versions. The first version consists of two stimulation and control time series, each time series being the average of a large number (≥2000) of replicates. The second version consists of obtaining ≥10 stimulation and control time series, each time series being the average of a moderate number (200-500) of replicates.

A variety of the first version consists of acquiring "alternate averages". Typically, two stimulation or control time series averages are acquired as, for example, 2000 successive replicates. Thus, time series 1 consists of the average of stimuli 1-2000 and time series 2 consists of the average of stimuli 2001-4000. With alternate averages time series 1 consists of the average of the odd numbered stimuli 1-3999 and time series 2 consists of the average of the even numbered stimuli 2-4000. The alternate average data acquisition technique is particularly useful when stimulating with a frequency of 20 Hz and using a data acquisition period of 100 ms. See Raabe, W., Walk, D., 2021. Slowly conducting potentials in human sensory nerves. J. Neurosci. Methods 351, 109045, which is incorporated by reference in its entirety, for additional information regarding the alternative average process.

The second version of acquiring time series data, consists of obtaining ≥10 stimulation and control time series, each time series being the average of a moderate number (200-500) of successive replicates. These data enable the analysis of multiple time series pairings with ALG045 and PS045. In the case of 10 stimulation (or control) time series, 45 different time series pairings can be analyzed with ALG045/PS045: TS1/TS2, TS1/TS3 . . . TS1/TS10, TS2/TS3, TS2/TS4, etc. The ALG045/PS045 data can be evaluated statistically, e.g., determination of the median for control and stimulation data time series. The median ALG045/PS045 of stimulation data has to exceed the maximum (or percentile-defined value) of the median of 45 control ALG045/PS045 to indicate a stimulation-evoked event, i.e., an event generated by the excitation of nerve fibers (Aδ- and C-fibers). See Raabe, W., Walk, D., 2022. Median amplitude and frequency analysis of sensory nerve responses to intraepidermal stimulation", J. Neurosci. Methods 365, 109377), which is incorporated by reference in its entirety, for additional information regarding the median analysis process.

Figure 12:
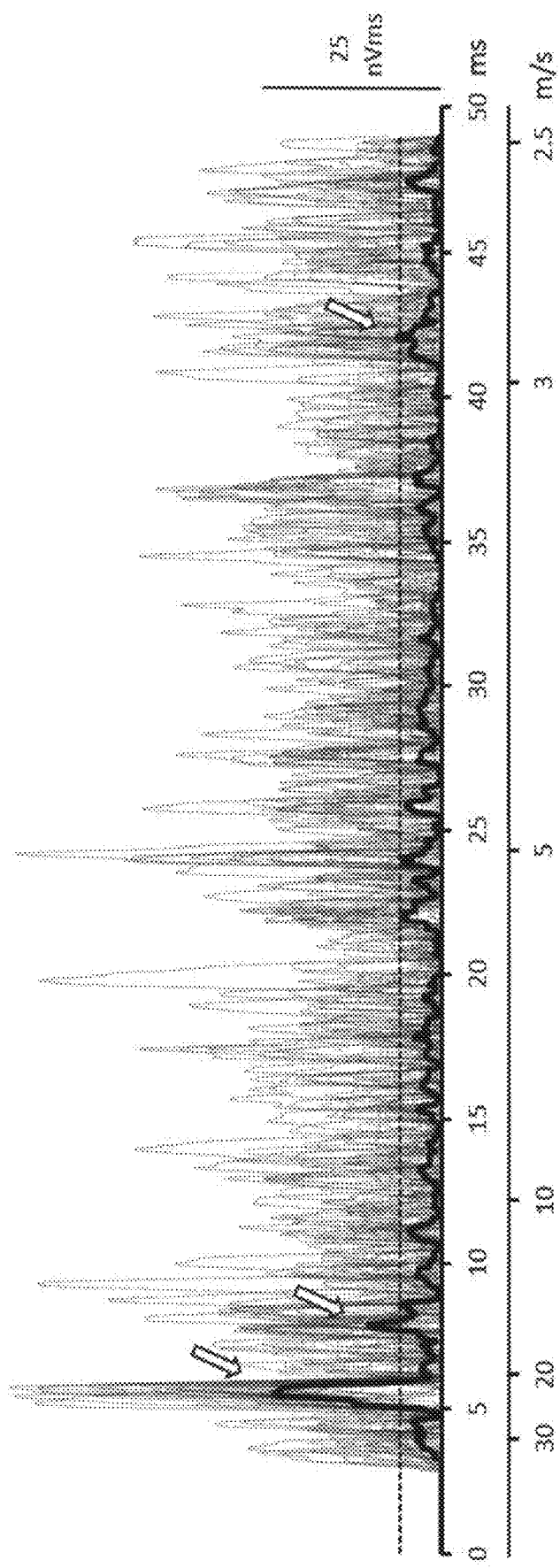
FIG. 12 illustrates median analysis of ALG045 derived from all 45 possible combinations of 10 time series.

FIG. 12 illustrates median analysis of 10 time series with ALG045 derived from all 45 possible combinations for each data point of the 10 time series, each time series is the average of 500 successive replicates. Ten averages yield 45 different record pairs for each data point for analysis with ALG045. Thin dotted lines show ALG045 for each data point of the 45 stimulation pairs derived from Stimulation #1-10 time series. The median of ALG045 from stimulation data is shown as thick black line. Dashed horizontal line marks the maximum of the median of ALG045 for 45 control time series record pairs (control record pairs not shown). Arrows point to the median of Stimulation ALG045 exceeding the maximum median of Control ALG045. Calibration bar on bottom is for conduction velocity in m/s. CVs calculated from peak latencies of median Stim ALG045 are 21.3, 14.9 and 2.8 m/s. Median analysis yields more ALG045 peaks exceeding the maximum of control ALG045 than ALG045 analysis of two alternate averages. Calibration bar in ms for latencies, in m/s for CVs (distance of 122 mm between stimulus and recording electrodes).

Figure 13:
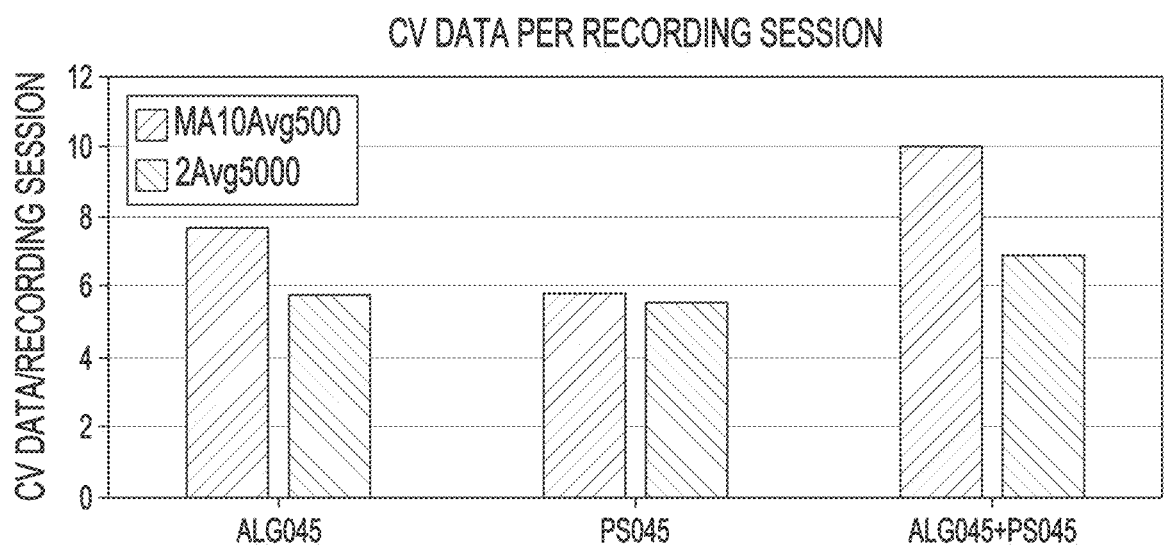
FIG. 13 illustrates that median analysis of ALG045 and PS045 of multiple (10) time series with a low number of replicates per average, 500, in all possible combinations yields more data than analysis of two time series with a large number of replicates per average, 5000.

FIG. 13 illustrates conduction velocity (CV) data yield by different methods for time series analysis. Median analysis of ALG045 and PS045 of multiple (10) time series with a moderate number of replicates per average (500) in all possible combinations yields more data than analysis of two time series with a large number of replicates per average (5000). Median Analysis is represented by black bars (MA10Avg500), where ALG045 and PS045 are obtained for all 45 possible pair combinations of 10 time series, each time series is the average of 500 replicates, and median ALG045 and PS045 of stimulation time series have to exceed the maximum median for control time series to identify a latency for CV calculation. Two time series with a large number of replicates per average (5000), 2Avg5000, is represented by striped bars, where ALG045 and PS045 are obtained for the time series 1 and 2, and each is the average of 5000 replicates. ALG045/PS045 exceeding the maximum of control ALG045/PS045 determines the latencies for CV calculation. (Time series data for MA10Avg500 and 2Avg5000 were identical.)

Control time series data are acquired in exactly the same way stimulation time series data are acquired. For example, stimulation time series data 1 and 2 are acquired as averages to successive stimuli 1-500 and stimuli 501-1000. The control time series data 1 and 2 have to be acquired in the same way. Otherwise, the analysis of control data time series with ALG045 and PS045 does not provide valid reference values (maxima, percentiles) for the analysis of stimulation time series with ALG045 and PS045.

Control time series data may be obtained from the same site used for obtaining stimulation time series data for ALG045 and PS045. Alternatively, control time series data for ALG045 and PS045 may be obtained from two or more different sites. ALG045 and PS045 data may be averaged before use, i.e., determination of the maxima or percentile data of control ALG045 and control PS045.

FIGS. 14-20 generally illustrate, by way of example and not limitation. various aspects of data acquisition. FIG. 14 illustrates sensory nerve conduction (SNCV) recording sessions to provide stimulation data ("STIM DATA") and SNCV recording sessions to provide Control Data ("CTRL DATA"). STIM DATA indicates that the record consists of responses to stimuli, and CTRL DATA indicates that the record consists of periods without stimuli. The EMG machine may be configured to digitally sample a signal at a sampling rate of 20 kHz. The signal may be sampled for duration between 40 ms to 1000 ms (e.g., "record period").

FIG. 15 illustrates a SNCV record, recorded by EMG equipment. The SNCV record with STIM DATA includes recorded electrical responses to stimuli, whereas the EMG record with CTRL data includes recorded electrical activity for a corresponding period of time without stimuli. The recorded electrical responses or recorded electrical activity includes a plurality of data points (e.g., data samples). Various groups may be formed from the recorded electrical responses in SNCV records. For example, FIG. 16 illustrates a group that includes a plurality of recorded electrical responses, where the recorded electrical responses include a plurality of data points. The group may include electrical responses (which also may be referred to as "replicates") from one or more of the SNCV records that were recorded by the EMG equipment. FIG. 17 illustrates averaging of the replicates, or electrical responses by corresponding data points for each of the replicates by averaging data points 1, averaging data points 2, averaging data points 3, etc., which converts the groups into an averaged electrical response group. The averaged electrical response groups are the first time series (TS1) and the second time series (TS2) when there are two averaged electrical response groups. When there are more than two averaged electrical response groups, the averaged electrical response groups may be used (e.g., via various combinations) to provide the first time series (TS1) and the second time series (TS2).

Figure 19:
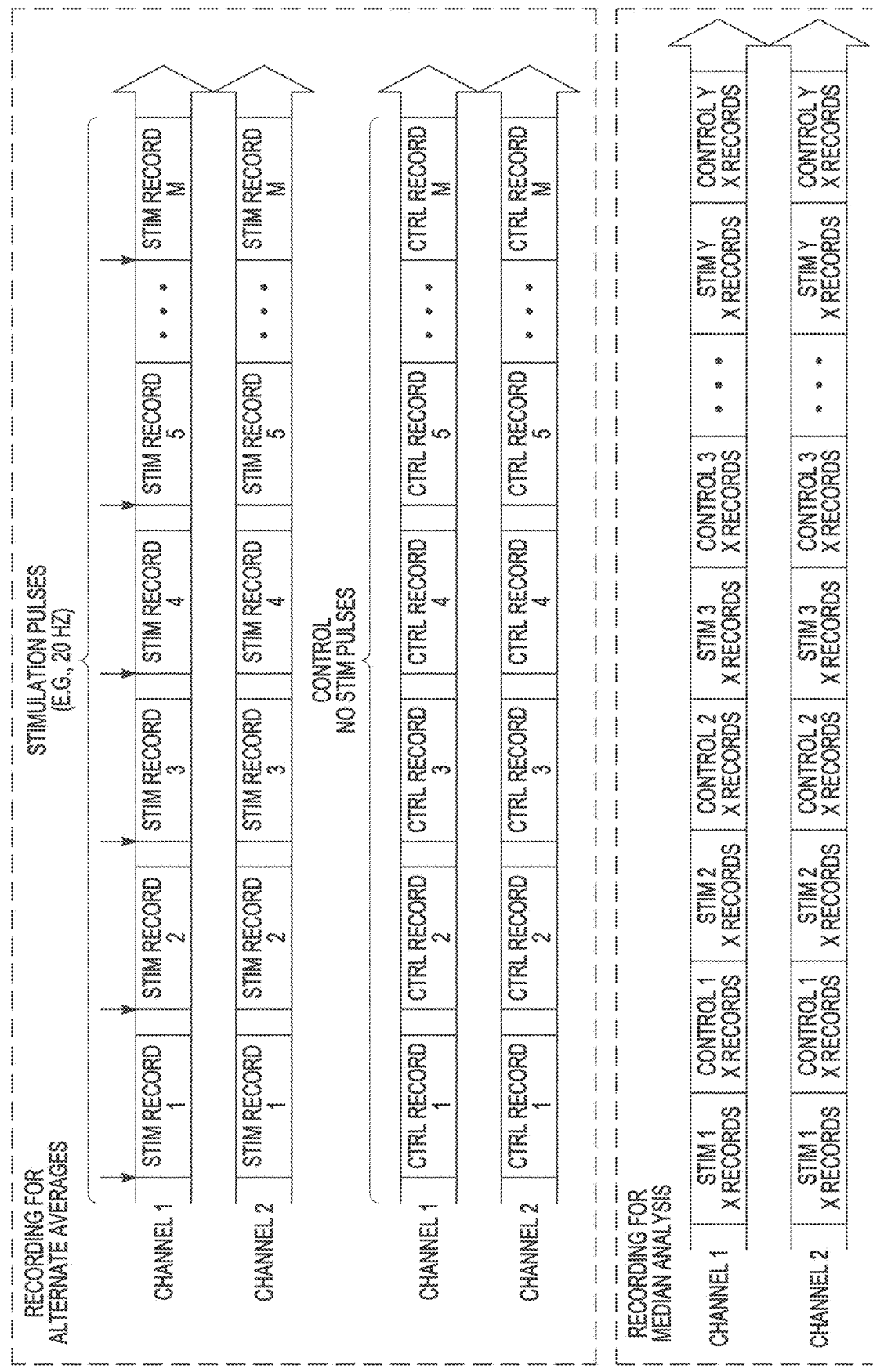
FIG. 19 illustrates, by way of example and not limitation, methods for obtaining stimulation and control records for use in creating one record pair using "two averages of a large number of replicates (1000-5000)" and in creating multiple record pairs of averages of a low/moderate number of replicates (250-500) for use with the "median analysis" technique.

FIG. 18 illustrates a first time series (TS1) and a second time series (TS2), which provide record pairs of data points (e.g., a first record pair: Data Point 1 in TS1 and Data Point 1 in TS2; a second record pair: Data Point 2 in TS2 and Data Point 2 in TS2, and the like). An algorithm may be executed using values for these record pairs. The algorithm may be used (e.g., Alg & ALG045) to find correlations of the data points in TS1 and TS2 in phase and amplitude, indicating that the potentials may be generated by the same set of single fiber action potentials. This algorithm may be applied to record pairs that have been created using successive averages, "alternate averages" and "median analysis" techniques. FIG. 19 illustrates, by way of example and not limitation, methods for obtaining stimulation and control records for use in creating a record pair using an "alternate averages" technique and using a "median analysis" technique. In the "alternate averages" technique, Stimulation Data may be recorded to capture responses to stimulation, which may be delivered as pulses at a static frequency such as, but not limited to, 20 Hz. Other pulses frequencies may be used, such as a frequency within the range of 1-20 Hz. Both of the two channels (Channel 1 and Channel 2) may be used to record a response signal for a period of time (e.g., about 50 ms) after each pulse to provide a plurality of records (i.e., STIM RECORDS 1-M for each channel). In the illustration, each of the M stim records corresponds to a recorded electrical response. As identified earlier, each record or response includes a plurality of data points (e.g., sampled data). By way of example and not limitation, over one thousand stimulation records for each channel may be recorded. Corresponding control data (CTRL RECORDS 1-M) may also be recorded, when no stimulation is being delivered, using record periods of time that correspond to the duration and timing of the STIM RECORDS. A record pair may be created using two groups of records, such as using odd numbered records for the first group, and the even numbered records for the second group. Thus, a large number of channel records may be recorded or determined using an EMG system, and stored in a file. The slow conducting fibers (e.g., Aδ- and C-fibers) may be analyzed using the large number of responses. In some embodiments, M=1000 such that 1000 records are recorded. However, the number of recorded records may be within a range of 2 records to 10,000 records. In the median analysis technique, each of the two EMG channels may be used to alternately implement STIM recording sessions/CTRL recording sessions to record X number of records with stimulation during each STIM recording session and record X number of records without stimulation during each CTRL recording session. The total number of recording sessions may be Y STIM recording sessions and Y CTRL recording sessions. A plurality of record pairs may be created for both STIM DATA and CTRL data using these Y recording sessions. In some embodiments, Y may equal 10 such that 10 separate recording sessions are used, and X equals 500 such that each record includes 500 records. However, the number of recording sessions (Y) may be within a range of 10 to 20, and the number of records per recording session may be within a range of 250 to 500.

Figure 20:
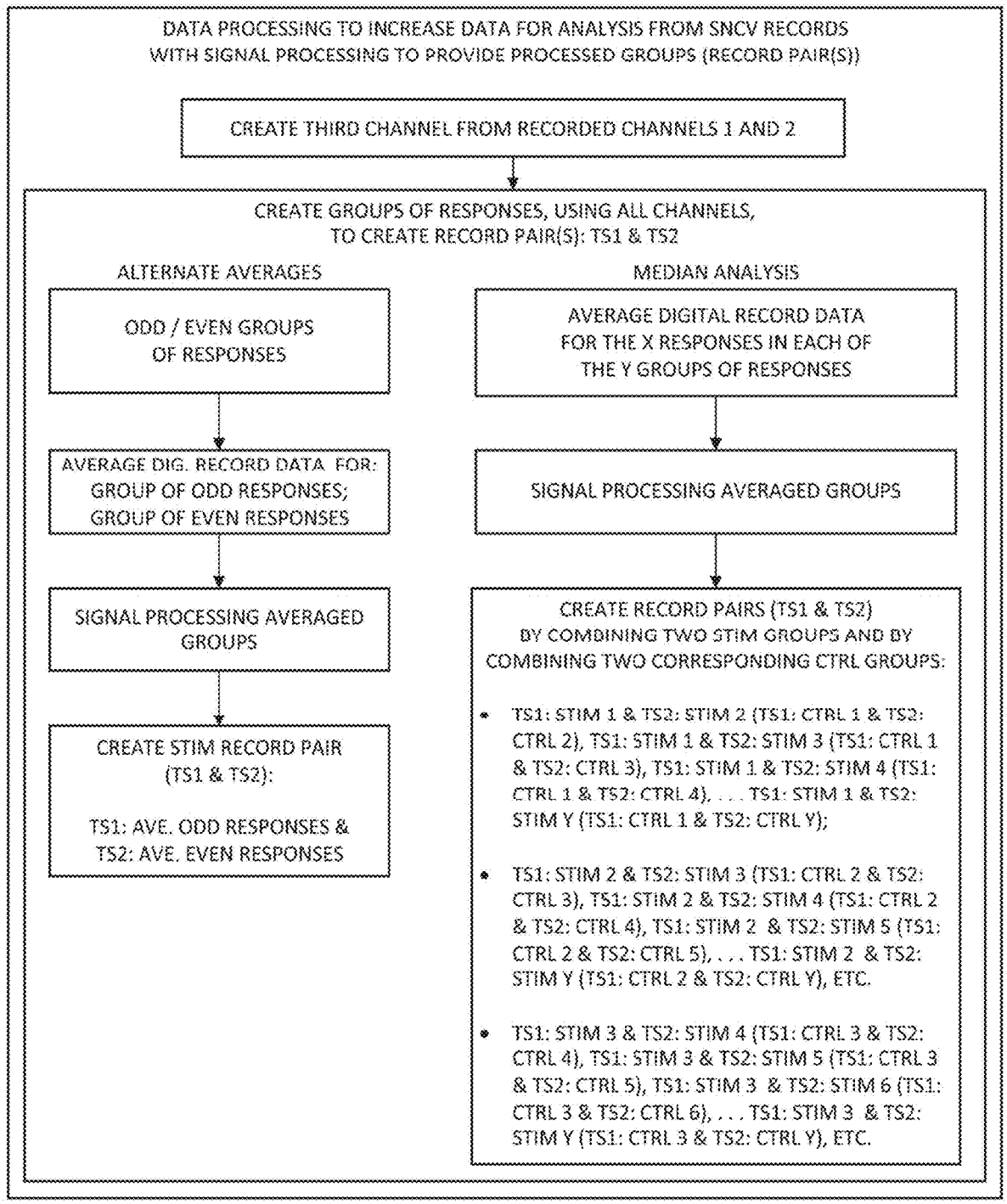
FIG. 20 illustrates a method for providing data processing, with signal processing, to increase data for analysis from the raw SNCV records that were recorded using the two EMG system channels.

FIG. 20 illustrates a method for providing data processing, with signal processing, to increase data for analysis from the raw SNCV records that were recorded using the two EMG machine channels. Thus, additional data may be analyzed without any requiring the patient to submit to a longer test. The method may create a third channel from the recorded channels 1 and 2. EMG systems may have two channels, such that each recording session may yield two digital time series a/b data for two channels. To obtain additional data without inserting more subdermal needles into the subject, a "third channel" may be constructed based on monopolar records from the other two channels using a difference between those monopolar records. For example, a first record may be obtained from a monopolar sensing between a first electrode R1 and a reference electrode Ref in channel 1, a second record may be obtained from a monopolar sensing between a second electrode R2 and the reference electrode Ref in channel 2, and a third record may be obtained from a difference between the two records (R1-R2). In another example, a first record may be obtained from bipolar sensing between electrodes R1 and R2 in channel 1, a second record may be obtained from bipolar sensing between electrodes R2 and R3, and a third record may be obtained from by adding the first and second records (R1-R2 plus R2-R3), to construct a third bipolar channel "R1-R3". The method may create groups of records, using all available channels (e.g., Channels 1 and 2, plus constructed Channel 3) to create record pairs. The figure illustrates both an Alternative Average technique for creating record pairs, and a Median Analysis technique for creating a plurality of record pairs. In the Alternative Average technique, the odd numbered records are grouped together and the even numbered records are grouped together. The digital record data (e.g., digital samples) are averaged for the group of odd numbered records, and are averaged for the group of even numbered records. The averaged groups (Average Odd/ Average Even) may be signal processed, and the first time series (TS1) and the second time series (TS2) may be created from the signal-processed, Average Odd and Average Even groups (Groups A and B). In the Median Analysis technique, the digital record data for the X responses are averaged in each of the Y groups of responses. Each of the averaged groups are signal processed. Records Pairs (Groups A and B) are created by combining two stimulation groups and by combining two corresponding control groups. Thus, a plurality of unique pairs may be created by unique combinations of groups. For example, a record pair may be created from groups Stim 1 & Stim 2, from groups Stim 1 & Stim 3, from groups Stim 1 & Stim 4, etc. For example, if there are 10 groups of records (Y=10), then there can be 45 different record pairs created from unique combinations of 2 for the 10 groups. For example, Group 1 may be uniquely combined with 9 groups (Groups 2-10), Group 2 may be uniquely combined with 8 groups (Groups 3-10), Group 3 may be uniquely combined with 7 groups (Groups 4-10), . . . and Group 9 may be uniquely combined with 1 group (Group 10) (i.e., 9+8+7+ . . . 1=45). These 45 record pairs may be combined to provide larger datasets for the two time series (TS1) and (TS2).

Figure 21:
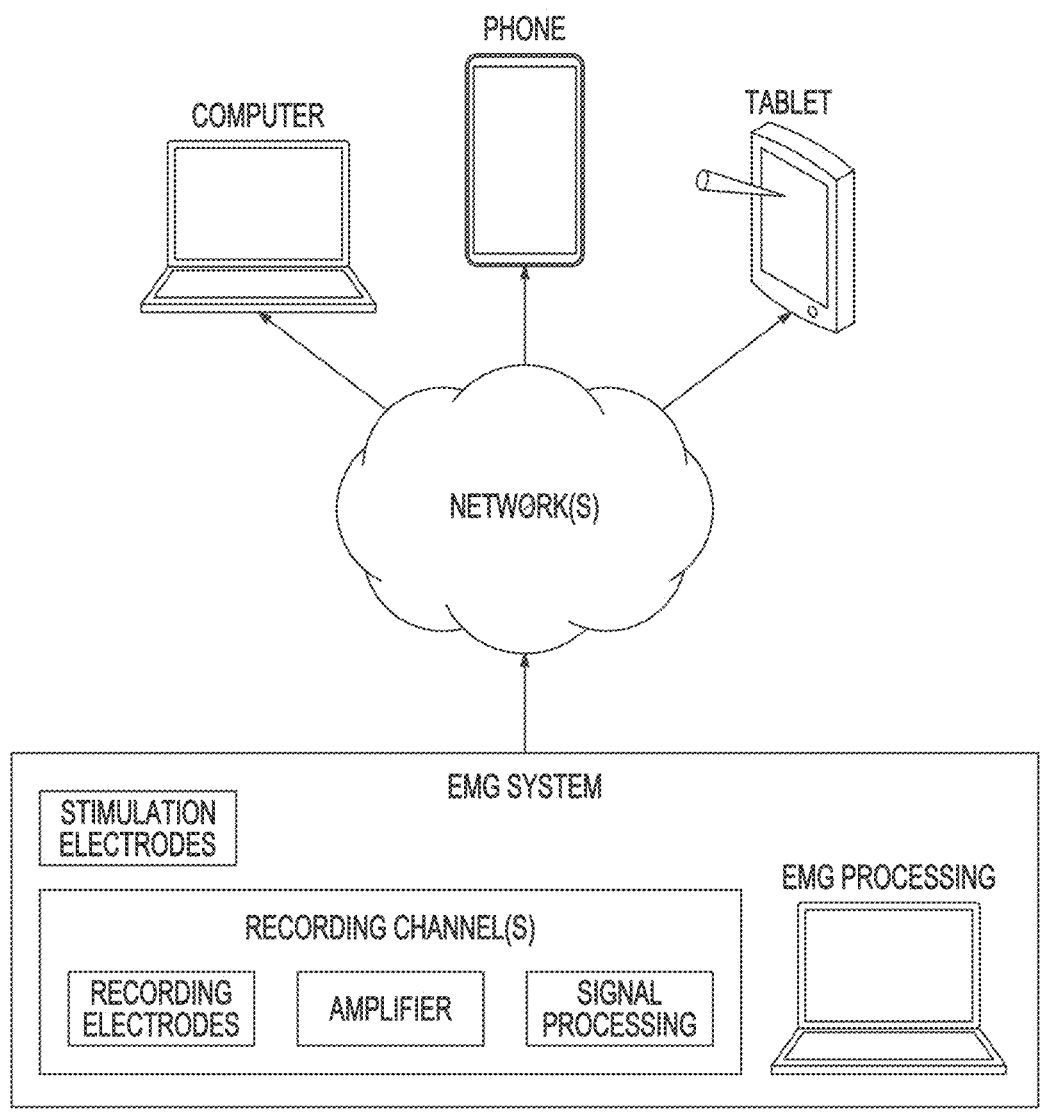
FIG. 21 illustrates, by way of example and not limitation, a system that may be used to analyze slow conducting fiber recordings from an EMG system.

FIG. 21 illustrates, by way of example and not limitation, a system that may be used to analyze slow conducting fiber recordings from an EMG system. The EMG system generally includes processing equipment, shown as a computer, stimulation electrodes for stimulating the subject, and recording channel(s) for recording responses to the stimulation. Each recording channel may include recording electrodes, an amplifier, and signal processing circuitry. Data files of the recordings from the EMG system may be uploaded to a Software As A Service (SAAS) system, which can perform all or a portion the analysis. The service may be a licensed service, in which a license is needed to access the service. In some embodiments, data from the EMG system is provided to another device in the network, such as the computer, tablet or phone, which may include a processor to execute instructions to apply the algorithms to the time series (TS1) and (TS2), and perform other functions discussed herein. The system may generate reports, which are transmitted to various user devices such as a laptop or desktop computer, a smart phone, or a tablet. The reports may include histograms of the distribution of conduction velocities.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventor also has contemplated examples in which only those elements shown or described are provided. Moreover, the present inventor has also contemplate examples using combinations or permutations of those elements shown or described.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method for examining sensory nerve conduction for small sensory nerve fibers, including Aδ-fibers and C-fibers, using an EMG system having electrodes, the EMG system being configured to deliver stimulation through a stimulation electrode and configured to record electrical potentials using a recording electrode, the method comprising:
    stimulating the small sensory nerve fibers using the stimulation electrode of the EMG system and creating recordings using the recording electrode of the EMG system, wherein the electrodes include an intra-epidermal stimulation electrode, a concentric planar electrode, or subdermal needles inserted into an epidermis:
    extracting information for electrical potentials generated by the small sensory nerve fibers. including the Aδ-fibers and the C-fibers, by:
    obtaining a first time series (TS1) and a second time series (TS2) of stimulation data corresponding to recordings that follow identical stimuli of neural tissue, and a first time series and a second time series of control data corresponding to recordings that do not follow the stimuli of the neural tissue, wherein TS1 and TS2 provide a plurality of pairs of data points such that each of the plurality of pairs include corresponding data points from both TS1 and TS2;
    analyzing the obtained time series by applying an algorithm (Alg) to the first time series (TS1) and the second time series (TS2) of stimulation data to create an algorithm value corresponding to each of the plurality of pairs of data points, wherein Alg=(|TS1|+|TS2|)/2−|TS1−TS2|, and the algorithm values include positive algorithm values;
    summing the positive algorithm values for a predetermined period of time (AlgVarTime) to create a signal;
    determining at least one peak in the signal; and
    determining a conduction velocity using a latency from a stimulus to the at least one peak in the signal and from a distance between the stimulating electrode used to deliver the stimulus and the recording electrode used to record the electrical potential; and
    generate and transmit a human-readable, conduction velocity report to a user device, the conduction velocity report including sensory nerve conduction information for the small sensory nerve fibers.

2. The method of claim 1, wherein the obtaining the first time series (TS1) and the second time series (TS2) of stimulation data includes:
    recording electrical responses to stimulating the small sensory nerve fibers, wherein each of the recorded electrical responses includes a plurality of data points acquired at equally spaced intervals;
    processing the recorded electrical responses to provide the first time series (TS1) and the second time series (T2), wherein the processing the recorded electrical responses includes:
    separating the recorded electrical responses into groups, wherein each of the groups includes a plurality of the recorded electrical responses;

converting each of the groups into averaged electrical response groups by averaging the plurality of responses in each of the groups, wherein the averaging the plurality of responses includes averaging corresponding ones of the plurality of data points in the plurality of responses, each of the averaged electrical response groups providing a plurality of averaged data points that correspond in number to the plurality of data points, wherein:

the averaged electrical response groups are the first time series (TS1) and the second time series (TS2) when there are two averaged electrical response groups; or the averaged electrical response groups are used to provide the first time series (TS1) and the second time series (TS2) when there are more than two averaged electrical response groups.

3. The method of claim 2, wherein:

the separating the recorded electrical responses into groups includes separating the recorded electrical responses into two groups, the two groups including a group of odd numbered responses and a group of even numbered responses; and the converting each of the groups into averaged electrical response groups includes:

averaging corresponding ones of the plurality of data points in the group of odd numbered responses to determine the first time series (TS1); and averaging corresponding ones of the plurality of data points in the group of even numbered responses to determine the second time series (TS2).

4. The method of claim 3, wherein each of the group of odd numbered responses and the group of even numbered responses includes more than 200 responses to stimulus.

5. The method of claim 2, wherein the recording electrical responses includes recording a plurality of records, wherein each of the plurality of records include a plurality of the recorded electrical responses, wherein the separating the recorded electrical responses into groups includes forming unique combinations of two records from the plurality of records to provide the first time series (TS1) and the second time series (TS2).

6. The method of claim 5, wherein the groups include at least 10 groups of electrical responses to stimulus.

7. The method of claim 2, wherein the stimulating the nerve includes stimulating the nerve at a frequency within a range from 0.5 Hz to 20 Hz using a device configured for stimulation of intraepidermal nerve fibers, and the recording electrical responses to stimulating the nerve includes using subdermal needle to obtain the recording.

8. The method of claim 1, wherein the first time series (TS1) and the second time series (TS2) are analyzed for amplitude using the algorithms (Alg), and wherein the predetermined period of time for summing the positive algorithm values is 0.45 ms.

9. The method of claim 2, wherein the first time series (TS1) and the second time series (TS2) are analyzed for power spectral density using a Hilbert transformation to determine a power spectra of frequencies for each of the averaged electrical response groups, the wherein the predetermined period of time for summing the positive algorithm values is 0.45 ms.

10. The method of claim 1, further comprising;

signal processing each of the first time series (TS1) and the second time series (TS2) for at least one variable to provide at least one pair of processed first time series (TS1) and second time series (TS2) for analysis, wherein the at least one variable includes amplitude or power spectral density, wherein each of the at least one pair of processed time series TS1 and TS2 include a plurality of pairs of data points.

11. The method of claim 10, wherein the signal processing each of the first time series (TS1) and the second time series (TS2) includes at least one of:

bandpass filtering to pass frequencies between about 500 Hz to about 1900 Hz;

notch filtering to remove excessive frequencies;

removing a stimulus artifact; or normalizing data.

12. The method of claim 1, wherein the predetermined period of time is within a range from 0.35 ms to 0.9 ms.

13. The method of claim 1, wherein the predetermined period of time is within a range from 0.40 ms to 0.50 ms.

14. The method of claim 1, wherein the predetermined period of time is 0.45 ms.

15. The method of claim 1, further comprising comparing the at least one peak in the signal to a threshold value to identify action potentials.

16. The method of claim 15, wherein the threshold value is determined using the first time series and the second time series of control data that do not follow stimuli of neural tissue.

17. The method of claim 16, further comprising applying the algorithm (Alg) to the first time series (TS1) and the second time series (TS2) of control data to create a control algorithm value corresponding to each of the plurality of pairs of data points, wherein the threshold is above or equal to 99% of a maximum control algorithm data.

18. The method of claim 1, further comprising receiving a file from a clinical group that includes at least one clinician, wherein the file includes recordings of electrical responses to stimulating the small sensory nerve fibers recorded using the EMG system, and the first time series (TS1) and the second time series (TS2) of stimulation data are obtained using the file, the method further comprising reporting the conduction velocity to the at least clinician via the user device.

19. The method of claim 18, wherein the reporting the conduction velocity includes reporting distributions of conduction velocities determined using the signal created by summing the positive algorithm values for the predetermined period of time (AlgVarTime).

20. The method of claim 18, further comprising entering a license granting permission to upload the file and to receive the reporting of the conduction velocity.

21. A non-transitory machine-readable medium including instructions, which when executed by a machine, cause the machine to implement a method for examining sensory nerve conduction for small sensory nerve fibers, including Aδ-fibers and C-fibers, using an EMG system having electrodes, the EMG system being configured to deliver stimulation through a stimulation electrode and configured to record electrical potentials using a recording electrode, wherein the method includes:

stimulating the small sensory nerve fibers using the stimulation electrode of the EMG system and creating recordings using the recording electrode of the EMG system, wherein the electrodes include an intra-epidermal stimulation electrode, a concentric planar electrode, or subdermal needles inserted into an epidermis;

extracting information for electrical potentials generated by the small sensory nerve fibers including the Aδ-fibers and the C-fibers, by:

obtaining a first time series (TS1) and a second time series (TS2) of stimulation data corresponding to recordings that follow identical stimuli of neural tissue, and a first time series and a second time series of control data corresponding to recordings that do not follow the stimuli of the neural tissue, wherein TS1 and TS2 provide a plurality of pairs of data points such that each of the plurality of pairs include corresponding data points from both TS1 and TS2;

analyzing the obtained time series by applying an algorithm (Alg) to the first time series (TS1) and the second time series (TS2) of stimulation data to create an algorithm value corresponding to each of the plurality of pairs of data points, wherein $Alg=(|TS1|+|TS2|)/2-|TS1-TS2|$, and the algorithm values include positive algorithm values;

summing the positive algorithm values for a predetermined period of time (AlgVarTime) to create a signal;

determining at least one peak in the signal; and determining a conduction velocity using a latency from a stimulus to the at least one peak in the signal and from a distance between the stimulating electrode used to deliver the stimulus and a recording electrode used to record the electrical potential; and generate and transmit a human-readable, conduction velocity report to a user device, the conduction velocity report including sensory nerve conduction information for the small sensory nerve fibers.

22. The non-transitory machine-readable medium of claim 21, wherein the obtaining the first time series (TS1) and the second time series (TS2) of stimulation data includes:

recording electrical responses to stimulating the small sensory nerve fibers, wherein each of the recorded electrical responses includes a plurality of data points acquired at equally spaced intervals, processing the recorded electrical responses to provide the first time series (TS1) and the second time series (T2), wherein the processing the recorded electrical responses includes:

separating the recorded electrical responses into groups, wherein each of the groups includes a plurality of the recorded electrical responses;

converting each of the groups into averaged electrical response groups by averaging the plurality of responses in each of the groups, wherein the averaging the plurality of responses includes averaging corresponding ones of the plurality of data points in the plurality of responses, each of the averaged electrical response groups providing a plurality of averaged data points that correspond in number to the plurality of data points, wherein:

the averaged electrical response groups are the first time series (TS1) and the second time series (TS2) when there are two averaged electrical response groups; or the averaged electrical response groups are used to provide the first time series (TS1) and the second time series (TS2) when there are more than two averaged electrical response groups.

* * * * *